(12) United States Patent
Schwink et al.

(10) Patent No.: US 7,241,787 B2
(45) Date of Patent: Jul. 10, 2007

(54) SUBSTITUTED N-CYCLOEXYLIMIDAZOLINONES, PROCESS FOR THEIR PREPARATION AND THEIR USE AS MEDICAMENTS

(75) Inventors: Lothar Schwink, Stadtallendorf (DE); Thomas Boehme, Ruesselsheim (DE); Matthias Gossel, Hofheim (DE); Siegfried Stengelin, Eppstein (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 12 days.

(21) Appl. No.: 11/042,713

(22) Filed: Jan. 25, 2005

(65) Prior Publication Data

US 2005/0176795 A1 Aug. 11, 2005

Related U.S. Application Data

(60) Provisional application No. 60/584,456, filed on Jun. 30, 2004.

(30) Foreign Application Priority Data

Jan. 25, 2004 (DE) .................. 10 2004 003 811

(51) Int. Cl.
| | |
|---|---|
| *A61K 31/551* | (2006.01) |
| *A61K 31/495* | (2006.01) |
| *A61K 31/439* | (2006.01) |
| *A61K 31/4439* | (2006.01) |
| *A61K 31/454* | (2006.01) |
| *A61K 31/4545* | (2006.01) |
| *A61K 31/4166* | (2006.01) |
| *C07D 243/08* | (2006.01) |
| *C07D 403/08* | (2006.01) |
| *C07D 453/00* | (2006.01) |
| *C07D 211/56* | (2006.01) |
| *C07D 211/06* | (2006.01) |
| *C07D 401/14* | (2006.01) |
| *C07D 401/04* | (2006.01) |
| *C07D 233/70* | (2006.01) |

(52) U.S. Cl. ................. 514/392; 514/218; 514/253.09; 514/254.05; 514/305; 514/326; 514/318; 540/575; 544/364; 544/370; 546/133; 546/194; 546/210; 546/274.1; 548/251; 548/255; 548/263.2; 548/311.1; 548/316.4

(58) Field of Classification Search ................. 548/251, 548/255, 263.2, 311.1, 316.4; 540/575; 544/364, 544/370; 546/133, 194, 210, 274.1; 514/218, 514/254.05, 305, 326, 318, 392, 253.09
See application file for complete search history.

(56) References Cited

U.S. PATENT DOCUMENTS

| | | | |
|---|---|---|---|
| 5,190,923 A | 3/1993 | Vincent et al. | |
| 5,276,049 A | 1/1994 | Himmelsbach et al. | |
| 5,478,942 A | 12/1995 | Himmelsbach et al. | |
| 5,650,424 A | 7/1997 | Himmelsbach et al. | |
| 5,681,841 A | 10/1997 | Himmelsbach et al. | |
| 5,852,192 A | 12/1998 | Himmelsbach et al. | |
| 5,880,284 A | 3/1999 | Himmelsbach et al. | |
| 6,221,633 B1 | 4/2001 | Ertl et al. | |
| 6,245,744 B1 | 6/2001 | Frick et al. | |
| 6,277,831 B1 | 8/2001 | Frick et al. | |
| 6,342,512 B1 | 1/2002 | Kirsch et al. | |
| 6,500,804 B2 | 12/2002 | Demuth et al. | |
| 6,890,905 B2 | 5/2005 | Demuth et al. | |

FOREIGN PATENT DOCUMENTS

| | | |
|---|---|---|
| WO | WO 94/18183 | 8/1994 |
| WO | WO 94/18184 | 8/1994 |
| WO | WO 97/26265 | 7/1997 |
| WO | WO 98/08871 | 3/1998 |
| WO | WO 98/19998 | 5/1998 |
| WO | WO 99/03861 | 1/1999 |
| WO | WO 99/15525 | 4/1999 |
| WO | WO 99/61431 | 12/1999 |

(Continued)

OTHER PUBLICATIONS

Asakawa, A., et. al., Cocaine-Amphetamine-Regulated Transcript Influences Energy Metabolism, Anxiety And Gastric Emptying in Mice, Hormone And Metabolic Research (2002, pp. 554-558, vol. 33, No. 9).

(Continued)

*Primary Examiner*—Kamal A. Gaeed
*Assistant Examiner*—Jason M. Nolan
(74) *Attorney, Agent, or Firm*—Barbara E. Kurys

(57) ABSTRACT

The invention relates to substituted N-cyclohexylheterocycles and to the physiologically tolerated salts and physiologically functional derivatives thereof, to processes for their preparation and to their use as medicaments.

Compounds of the formula I, $$R1\diagdown K\diagup E\diagdown X\diagup N\diagup \underset{\underset{O}{\|}}{C}\diagdown N\diagup \text{(cyclohexyl with A-Q and }(R2)_n\text{)}$$
with $D=G$ on the imidazolinone ring in which the radicals have the stated meanings, and the physiologically tolerated salts thereof, and process for their preparation are described. The compounds bring about for example a weight reduction in mammals and are suitable for example for the prevention and treatment of obesity and diabetes.

15 Claims, No Drawings

FOREIGN PATENT DOCUMENTS

| | | |
|---|---|---|
| WO | WO 99/67278 | 12/1999 |
| WO | WO 99/67279 | 12/1999 |
| WO | WO 00/40569 | 7/2000 |
| WO | WO 00/63208 | 10/2000 |
| WO | WO 00/66585 | 11/2000 |
| WO | WO 00/71549 | 11/2000 |
| WO | WO 00/78312 | 12/2000 |
| WO | WO 01/04146 | 1/2001 |
| WO | WO 01/09111 | 2/2001 |
| WO | WO 01/21577 | 3/2001 |
| WO | WO 01/83451 | 11/2001 |
| WO | WO 01/85695 | 11/2001 |
| WO | WO 01/91752 | 12/2001 |
| WO | WO 01/94300 | 12/2001 |
| WO | WO 02/002744 | 1/2002 |
| WO | WO 02/06245 | 1/2002 |
| WO | WO 02/10146 | 2/2002 |
| WO | WO 02/38541 | 5/2002 |
| WO | WO 02/50027 | 6/2002 |
| WO | WO 02/057233 | 7/2002 |
| WO | WO 02/089729 | 11/2002 |
| WO | WO 02/096864 | 12/2002 |
| WO | WO 03/035624 | 5/2003 |
| WO | WO 03/040174 | 5/2003 |
| WO | WO 03/045313 | 6/2003 |
| WO | WO 03/057220 | 7/2003 |
| WO | WO 03/084922 | 10/2003 |
| WO | WO 03/084923 | 10/2003 |
| WO | WO 03/087044 | 10/2003 |
| WO | WO 03/097047 | 11/2003 |
| WO | WO 03/104188 | 12/2003 |
| WO | WO 2004/011438 | 2/2004 |

OTHER PUBLICATIONS

Borowsky, B., et. al., Antidepressant, Anxiolytic and Anorectic Effects of a Melanin-Concentrating Hormone-1 Receptor Antagonist, Nature Medicine (2002, pp. 825-830, vol. 8, No. 8).

Lee, D.W., et. al., Leptin Agonists As A Potential Approach To The Treatment Of Obesity, Drugs Of The Future (2001, pp. 873-881, vol. 26, Issue 9).

Qu, D., et. al., A Role For Melanin-Concentrating Hormone In The Central Regulation Of Feeding Behaviour, Nature (1996, pp. 243-247, vol. 380).

Zunft, H.J., et. al., Carob Pulp Preparation for Treament of Hypercholesterolemia, Advances in Natural Therapy (2001, pp. 230-236, vol. 18, No. 5).

Hervieu, G., et. al., Melanin-concentrating hormone functions in the nervous system: food intake and stress, Expert Opin (2003, pp. 495-511, vol. 7, No. 4).

Okada, H., et. al., Synthesis And Antitumor Activities Of Prodrugs Of Benzoylphenylureas, Chem. Pharm. Bull (1994, 57-61, vol. 42, No. 1).

Kawafuchi, H., et. al., Novel Access to Cyclohexane-1,4-Diones and 1,4-Hydroquinones via Radical 1,2-Acyl Rearrangement on 2-(Halomethyl) Cyclopentane-1,3-Diones Using Cobaloxime-Mediated Electroreduction or Tributyltin Hydride, Tetrahedron Letters (2002, pp. 2051-2054, vol. 43).

Beauhaire, J., et. al., Indentification And Synthesis Of Sordidin, a Male Pheromone Emitted by Cosmopolites Sordidus, Tetrahedron Letter (1995, pp. 1043-1046, vol. 36, No. &).

Pereira-Da-Silva, M., et. al., Hypothalamic Melanin-Concentrating Hormone Is Induced by Cold Exposure and Participates in the Control of Energy Expenditure in Rats, Endocrinology (2003, pp. 4831-4840, vol. 144).

Nakamura, M., et. al., Enantioselective Synthesis of alpha-Substituted Ketones by Asymmetric Addition of Chiral Zinc Enamides to 1-Alkenes, J. Am. Chem. Soc. (2003, pp. 6362-6363, vol. 125).

Shimada, M., et. al., Mice Lacking Melanin-Concentrating Hormone Are Hypophagic And Lean, Nature (1998, pp. 670-674, vol. 396).

Chen, Y., et. al., Targeted Disruption of the Melanin-Concentrating Hormone Receptor-1 Results in Hyperphagia and Resistance to Diet-Induced Obesity, Endocrinology (2002, pp. 2469-2477, vol. 143).

SUBSTITUTED N-CYCLOEXYLIMIDAZOLINONES, PROCESS FOR THEIR PREPARATION AND THEIR USE AS MEDICAMENTS

The invention relates to substituted N-cyclohexylheterocycles and to the physiologically tolerated salts and physiologically functional derivatives thereof.

Compounds similar in their overall structure to the heteroatom-substituted cyclohexylimidazolinones described herein and having a pharmacological effect have been described in the prior art. Thus, for example, WO 03/057220 describes imidazolone derivatives (cyclic urea derivatives) having 5-$HT_{2c}$ receptor activity which can be used for the treatment of disorders of the central nervous system, such as depression and anxiety, and gastrointestinal complaints. These compounds each have an aromatic group as substituent on the central nitrogen atoms.

The non-prior-published application with earlier priority and the file number DE 102 33 817.5 (WO 2004/11438) likewise relates to cyclic urea derivatives each having an aromatic group as substituent on the central nitrogen atoms, where one of the aromatic groups has at least one nitrogen-containing substituent. The aryl-substituted cyclic urea derivatives have an MCH-modulatory effect. The compounds are suitable for example as anorectic agents.

In addition, EP-A 0 503 548 and EP-A 0 587 134 describe similar compounds having a pharmacological effect. EP 0 503 548 and EP 0 587 134 relate to cyclic urea derivatives which have aggregation-inhibiting effects, to medicaments comprising these compounds and to processes for their preparation.

Compounds having an MCH-antagonistic effect for the treatment of obesity are described in the prior art (examples: WO 2001021577, WO 2003035624, WO 2002089729, WO 2002006245, WO 2002002744, WO 2002057233, WO 2003045313, WO 2003097047, WO 2002010146, WO 2003087044).

The invention was based on the object of providing compounds which bring about a weight reduction in mammals and which are suitable for the prevention and treatment of obesity and diabetes.

A series of compounds which modulate the activity of MCH receptors has surprisingly been found. The compounds are distinguished in particular by antagonism of the MCH1R.

The invention therefore relates to compounds of the formula I,

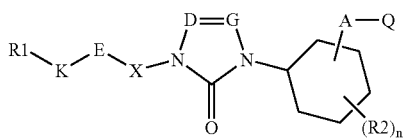

in which the meanings are

R1 H, ($C_1$–$C_8$)-alkyl, ($C_1$–$C_4$)-alkoxy-($C_1$–$C_4$)-alkyl, ($C_3$–$C_8$)-alkenyl, ($C_3$–$C_8$)-alkynyl, a 3 to 10-membered mono-, bi- or spirocyclic ring which may include 0 to 4 heteroatoms selected from the group of oxygen, nitrogen and sulfur, where the ring system may be additionally substituted by F, Cl, Br, $CF_3$, $NO_2$, CN, ($C_1$–$C_6$)-alkyl, O—($C_1$–$C_8$)-alkyl, S—($C_1$–$C_8$)-alkyl, ($C_1$–$C_4$)-alkoxy-($C_1$–$C_4$)-alkyl, ($C_0$–$C_8$)-alkylene-aryl, oxo, CO(R3), CON(R4)(R5), hydroxy, hydroxy-($C_1$–$C_4$)-alkyl, COO (R6), N(R7)CO($C_1$–$C_6$)-alkyl, N(R8)(R9) or $SO_2CH_3$;

R3, R4, R5, R6, R7, R8, R9, independently of one another H, ($C_1$–$C_6$)-alkyl;

K a group of the formula —(CR10OR11)$_z$—, in which one or more —(CR10R11)-groups may be replaced by Z to result in a chemically reasonable radical, a bond, C≡C, C=C;

Z O, CO, N(R59), S, SO, $SO_2$;

R10, R11 independently of one another H, ($C_1$–$C_8$)-alkyl, hydroxy-($C_1$–$C_4$)-alkyl, hydroxy, ($C_1$–$C_4$)-alkoxy-($C_1$–$C_4$)-alkyl, where R10 and R11 in the z groups may in each case have the same or different meanings;

z 1, 2, 3, 4, 5, 6;

R59 H, ($C_1$–$C_8$)-alkyl;

E 3–14 membered bivalent carbo- or heterocyclic ring structure having 0–4 heteroatoms from the group of N, O and S, which may optionally have substituents from the group of H, F, Cl, Br, I, OH, $CF_3$, $NO_2$, CN, $OCF_3$, oxo, O—($C_1$–$C_6$)-alkyl, O—($C_1$–$C_4$)-alkoxy-($C_1$–$C_4$)-alkyl, S—($C_1$–$C_6$)-alkyl, ($C_1$–$C_6$)-alkyl, ($C_2$–$C_6$)-alkenyl, ($C_3$–$C_8$)cycloalkyl, O—($C_3$–$C_8$)cycloalkyl, ($C_3$–$C_8$)cycloalkenyl, O—($C_3$–$C_8$)cycloalkenyl, ($C_2$–$C_6$)-alkynyl, ($C_0$–$C_8$)-alkylene-aryl, O—($C_0$–$C_8$)-alkylene-aryl, S-aryl, N(R12)(R13), $SO_2$—$CH_3$, COOH, COO—($C_1$–$C_6$)-alkyl, CON(R14)(R15), N(R16)CO(R17), N(R18)$SO_2$(R19), CO(R20) and be mono or bicyclic; preferably 3–14 membered bivalent carbo- or heterocyclic ring structure with 0–4 heteroatoms from the group of N, O and S, which may optionally have substituents from the group of H, F, Cl, Br, I, OH, $CF_3$, $NO_2$, CN, $OCF_3$, oxo, O—($C_1$–$C_6$)-alkyl, O—($C_1$–$C_4$)-alkoxy-($C_1$–$C_4$)-alkyl, S—($C_1$–$C_6$)-alkyl, ($C_1$–$C_6$)-alkyl, ($C_2$–$C_6$)-alkenyl, N(R12)(R13), $SO_2$—$CH_3$, N(R16)CO(R17), N(R18)$SO_2$ (R19), CO(R20) and be mono- or bicyclic;

R12, R13, R14, R15, R16, R18 independently of one another H, ($C_1$–$C_8$)-alkyl;

or

R12 and R13, R14 and R15 independently of one another, optionally together with the nitrogen atom to which they are bonded, a 5–6 membered ring which, apart from the nitrogen atom, may also include 0–1 further heteroatoms from the group of N—($C_1$–$C_6$)-alkyl, oxygen and sulfur;

R17, R19, R20 independently of one another H, ($C_1$–$C_8$)-alkyl, aryl;

X a bond, a group of the formula —(CR21R22)$_y$—, in which one or more —(CR21 R22)— groups may be replaced by Y to result in a chemically reasonable radical;

Y O, CO, N(R23), S, SO, $SO_2$;

R21, R22 independently of one another H, ($C_1$–$C_4$)-alkyl, where R21 and R22 in the y groups may in each case have the same or different meanings;

y 1, 2, 3, 4, 5, 6; preferably 2, 3, 4, 5, 6;

R23 H, ($C_1$–$C_8$)-alkyl;

D, G CH or N;

R2 OH, O—($C_1$–$C_6$)-alkyl, O—($C_1$–$C_4$)-alkoxy-($C_1$–$C_4$)-alkyl, ($C_1$–$C_6$)-alkyl;

n 0, 1, 2, 3, 4;

Q N(R24)(R25), a 3 to 8-membered ring which may include 0 to 3 heteroatoms selected from the group of oxygen, nitrogen and sulfur, where the ring system may additionally be substituted by ($C_0$–$C_4$)-alkylene-N(R24)(R25), preferably N(R24)(R25); F, Cl, Br, $CF_3$, $NO_2$, CN, ($C_1$–$C_6$)-alkyl, O—($C_1$–$C_8$)-alkyl, ($C_1$–$C_4$)-alkoxy-($C_1$–$C_4$)-alkyl, ($C_0$–$C_8$)-alkylene-aryl, oxo, CO(R26), CON(R27)(R28), hydroxy, hydroxy-$(C_1–C_4)$-alkyl, COO (R29), N(R30)CO$(C_1–C_6)$-alkyl or $SO_2CH_3$;

R26, R27, R28, R29, R30 independently of one another H, $(C_1–C_6)$-alkyl;

A a group of the formula —(C(R31)(R32))$_m$—, in which 0–2 members may be replaced by an element from the group of O, S, N(R33), CO, $SO_2$;

m 0, 1, 2, 3, 4, 5;

R31, R32, R33 independently of one another H, $(C_1–C_6)$-alkyl, aryl;

R24, R25 independently of one another H, $(C_1–C_8)$-alkyl, —(CR34R35)$_o$—R36, $(C_1–C_4)$-alkoxy-$(C_1–C_4)$-alkyl, $(C_3–C_8)$-alkenyl, $(C_3–C_8)$-alkynyl, CO—$(C_1–C_8)$-alkyl, —CO—(CH$_2$)$_o$—R36, CO(C(R37)(R38))$_q$N(R39)(R40), CO(C(R41)(R42))$_s$O(R43); or R24 and R25 form together with the nitrogen atom to which they are bonded a 4 to 10-membered mono-, bi- or spirocyclic ring which, apart from the nitrogen atom, may include 0 to 4 additional heteroatoms selected from the group of oxygen, nitrogen and sulfur, where the heterocyclic ring system may additionally be substituted by F, Cl, Br, $CF_3$, $NO_2$, CN, $(C_1–C_6)$-alkyl, O—$(C_1–C_8)$-alkyl, $(C_1–C_4)$-alkoxy-$(C_1–C_4)$-alkyl, hydroxy-$(C_1–C_4)$-alkyl, $(C_0–C_8)$-alkylene-aryl, oxo, CO(R44), CON(R45)(R46), hydroxy, COO(R47), N(R48)CO$(C_1–C_6)$-alkyl, N(R49)(R50) or $SO_2CH_3$;

o 0, 1, 2, 3, 4, 5, 6;

q, s independently of one another 0, 1, 2, 3, 4;

R34, R35 independently of one another H, $(C_1–C_8)$-alkyl, hydroxy-$(C_1–C_4)$-alkyl, OH, $(C_1–C_4)$-alkoxy-$(C_1–C_4)$-alkyl;

R37, R38, R39, R40, R41, R42, R43, R44, R45, R46, R47, R48, R49, R50 independently of one another H, $(C_1–C_6)$-alkyl;

R39 and R40, R45 and R46, R49 and R50 independently of one another, optionally together with the nitrogen atom to which they are bonded a 5–6 membered ring which, apart from the nitrogen atom, may also include 0–1 further heteroatoms from the group of N-$(C_1–C_6)$-alkyl, oxygen and sulfur;

R36 OH, O—$(C_1–C_6)$-alkyl, O—$(C_0–C_8)$-alkylene-aryl, CON(R51)(R52), N(R53)(R54), 3–12 membered mono-, bi- or spirocyclic ring which may comprise one or more heteroatoms from the group of N, O and S, and the 3–12 membered ring may comprise further substituents such as F, Cl, Br, I, OH, $CF_3$, $NO_2$, CN, $OCF_3$, oxo, O—$(C_1–C_6)$-alkyl, $(C_1–C_4)$-alkoxy-$(C_1–C_4)$-alkyl, S—$(C_1–C_6)$-alkyl, $(C_1–C_6)$-alkyl, $(C_2–C_6)$-alkenyl, $(C_3–C_8)$cycloalkyl, O—$(C_3–C_8)$cycloalkyl, $(C_3–C_8)$cycloalkenyl, O—$(C_3–C_8)$cycloalkenyl, $(C_2–C_6)$-alkynyl, O—$(C_0–C_8)$-alkylene-aryl, $(C_0–C_8)$-alkylene-aryl, N(R55)(R56), CO$(C_1–C_6)$-alkyl, COO(R57) and S(O)$_u$ (R58);

u 0, 1, 2;

R51, 52 independently of one another H, $(C_1–C_8)$-alkyl, $(C_2–C_6)$-alkenyl, $(C_0–C_8)$-alkylene-aryl;

R53, R54 independently of one another H, $(C_1–C_6)$-alkyl;

R55, R56 independently of one another H, $(C_1–C_8)$-alkyl;

R57 H, $(C_1–C_8)$-alkyl, $(C_2–C_6)$-alkenyl, $(C_0–C_8)$-alkylene-aryl;

R58 $(C_1–C_6)$-alkyl, 5–10 membered aromatic ring system which may comprise 0–2 further heteroatoms from the group of nitrogen, oxygen and sulfur and be substituted by F, Cl, Br, $CF_3$, $NO_2$, CN, $(C_1–C_8)$-alkyl, O—$(C_1–C_8)$-alkyl;

and the physiologically tolerated salts thereof.

The radicals R1 and R2, the index n and the groups K, E, X, D=G, Q and A preferably have, independently of one another, the following meanings:

R1 H, $(C_1–C_8)$-alkyl, $(C_1–C_4)$-alkoxy-$(C_1–C_4)$-alkyl, a 3–8 membered monocyclic ring which may include 0 to 3 heteroatoms selected from the group of oxygen, nitrogen and sulfur, where the ring system may additionally be substituted by F, Cl, Br, $(C_1–C_6)$-alkyl, O—$(C_1–C_8)$-alkyl, $(C_1–C_4)$-alkoxy-$(C_1–C_4)$-alkyl;

preferably $(C_1–C_8)$-alkyl, a 3–7 membered monocyclic ring which may include 0 to 2 heteroatoms selected from the group of oxygen, nitrogen and sulfur, where the ring system may additionally be substituted by F, Cl, Br, $(C_1–C_6)$-alkyl, O—$(C_1–C_8)$-alkyl;

particularly preferably $(C_1–C_6)$-alkyl, $(C_3–C_7)$-cycloalkyl and phenyl.

K O, a bond, C≡C, CO, $OCH_2$, $OCH_2CH_2$,
preferably O, a bond;
particularly preferably O.

E a 5–6 membered monocyclic bivalent carbo- or heterocyclic ring structure having 0–2 heteroatoms from the group of N, O and S, which may optionally have substituents from the group of H, F, Cl, Br, oxo, O—$(C_1–C_6)$-alkyl, O—$(C_1–C_4)$-alkoxy-$(C_1–C_4)$-alkyl, $(C_1–C_6)$-alkyl;
preferably a para- or meta-substituted 6 membered aromatic or heteroaromatic ring structure which may optionally have 1–2 substituents from the group of F, Cl, Br, O—$(C_1–C_6)$-alkyl, $(C_1–C_6)$-alkyl;
particularly preferably an unsubstituted 1,4-phenylene or 2,5-pyridylene unit.

X a bond, $CH_2CH_2$, $CH_2CH_2CH_2$, $OCH_2CH_2$;
preferably a bond, $CH_2CH_2$;
particularly preferably a bond.

D=G CH=CH, CH=N, N=CH;
preferably CH=CH, N=CH;
particularly preferably CH=CH.

R2 OH, O—$(C_1–C_6)$-alkyl, $(C_1–C_6)$-alkyl;
preferably OH, $(C_1–C_6)$-alkyl;
particularly preferably $(C_1–C_6)$-alkyl.

n 0, 1, 2;
preferably 0, 1;
particularly preferably 0.

Q a group of the formula N(R24)(R25), a 3 to 8-membered ring having 0–3 heteroatoms from the group of oxygen, nitrogen and sulfur, where the ring system may additionally be substituted by N(R24)(R25), F, Cl, Br, $CF_3$, $NO_2$, CN, $(C_1–C_6)$-alkyl, O—$(C_1–C_8)$-alkyl, $(C_1–C_4)$-alkoxy-$(C_1–C_4)$-alkyl, $(C_0–C_8)$-alkylene-aryl, oxo, CO(R26), CON(R27)(R28), hydroxy, COO(R29), N(R30)CO $(C_1–C_6)$-alkyl, or $SO_2CH_3$;
preferably a group of the formula N(R24)(R25), a nitrogen-containing 4 to 8-membered ring which, apart from the nitrogen atom, may also comprise further 0–2 heteroatoms from the group of oxygen, nitrogen and sulfur, and where the ring system may additionally be substituted by N(R24)(R25), F, $(C_1–C_6)$-alkyl, O—$(C_1–C_8)$-alkyl, $(C_1–C_4)$-alkoxy-$(C_1–C_4)$-alkyl, $(C_0–C_8)$-alkylene-aryl, oxo, CO(R26), N(R30)CO $(C_1–C_6)$-alkyl, or $SO_2CH_3$;
particularly preferably a group of the formula N(R24) (R25), a nitrogen-containing 5 to 8-membered ring which, apart from the nitrogen atom, may also comprise further 0–1 heteroatoms from the group of oxygen, nitrogen and sulfur, and where the ring system may additionally be substituted by N(R24)(R25), ($C_1$–$C_6$)-alkyl, O—($C_1$–$C_8$)-alkyl, ($C_0$–$C_8$)-alkylene-aryl, oxo, CO(R26), N(R30)CO($C_1$–$C_6$)-alkyl, or $SO_2CH_3$;

very particularly preferably a group of the formula N(R24)(R25), a nitrogen-containing 5 to 8-membered ring which, apart from the nitrogen atom, may also comprise further 0–1 heteroatoms from the group of oxygen, nitrogen and sulfur, and where the ring system may additionally be substituted by N(R24)(R25), ($C_1$–$C_6$)-alkyl or N(R30)CO($C_1$–$C_6$)-alkyl;

R24, R25 independently of one another H, ($C_1$–$C_8$)-alkyl, —(CR34R35)$_o$—R36, ($C_1$–$C_4$)-alkoxy-($C_1$–$C_4$)-alkyl, ($C_3$–$C_8$)-alkenyl, ($C_3$–$C_8$)-alkynyl, CO—($C_1$–$C_8$)-alkyl, —CO—($CH_2$)$_o$—R36, or R24 and R25 form together with the nitrogen atom to which they are bonded a 4 to 8-membered monocyclic ring which, apart from the nitrogen atom, may include 0 to 2 additional heteroatoms selected from the group of oxygen, nitrogen and sulfur, where the heterocyclic ring system may additionally be substituted by F, ($C_1$–$C_6$)-alkyl, O—($C_1$–$C_8$)-alkyl, ($C_1$–$C_4$)-alkoxy-($C_1$–$C_4$)-alkyl, hydroxy-($C_1$–$C_4$)-alkyl, ($C_0$–$C_8$)-alkylene-aryl, oxo, CO(R44), N(R48)CO ($C_1$–$C_6$)-alkyl, N(R49)(R50) or $SO_2CH_3$;

preferably independently of one another H, ($C_1$–$C_8$)-alkyl, ($C_1$–$C_4$)-alkoxy-($C_1$–$C_4$)-alkyl, CO—($C_1$–$C_8$)-alkyl, or R24 and R25 form together with the nitrogen atom to which they are bonded a 4 to 8-membered monocyclic ring which, apart from the nitrogen atom, may include 0 or 1 additional heteroatoms selected from the group of oxygen, nitrogen and sulfur, where the heterocyclic ring system may additionally be substituted by ($C_1$–$C_6$)-alkyl, N(R48)CO($C_1$–$C_6$)-alkyl or N(R49)(R50);

particularly preferably independently of one another H, ($C_1$–$C_8$)-alkyl, CO—($C_1$–$C_8$)-alkyl, or R24 and R25 form together with the nitrogen atom to which they are bonded a 5 to 7-membered monocyclic ring which, apart from the nitrogen atom, may also comprise a further nitrogen atom, where the heterocyclic ring system may additionally be substituted by ($C_1$–$C_6$)-alkyl, N(R48)CO($C_1$–$C_6$)-alkyl or N(R49)(R50);

o 0, 1, 2, 3, 4, 5;
preferably 0, 1, 2, 3, 4;
particularly preferably 0, 1, 2, 3;

R34, R35 independently of one another H, ($C_1$–$C_8$)-alkyl, hydroxy-($C_1$–$C_4$)-alkyl, OH, ($C_{1-4}$)-alkoxy-($C_1$–$C_4$)-alkyl;
preferably H, ($C_1$–$C_8$)-alkyl;
particularly preferably H;

R44, R48, R49, R50 independently of one another H, ($C_1$–$C_6$)-alkyl;

R49 and R50 optionally together with the nitrogen atom to which they are bonded a 5–6 membered ring which, apart from the nitrogen atom, may also include 0–1 further heteroatoms from the group of N-($C_1$–$C_6$)-alkyl, oxygen and sulfur;

R36 O—($C_1$–$C_6$)-alkyl, 5–8 membered monocyclic ring which may comprise 0–2 heteroatoms from the group of N, O and S, and the 5–8 membered ring may comprise further substituents such as F, Cl, Br, oxo, O—($C_1$–$C_6$)-alkyl, ($C_1$–$C_4$)-alkoxy-($C_1$–$C_4$)-alkyl, ($C_1$–$C_6$)-alkyl, ($C_0$–$C_8$)-alkylene-aryl, N(R55)(R56);
preferably O—($C_1$–$C_6$)-alkyl;

R55, R56 independently of one another H, ($C_1$–$C_8$)-alkyl;
R26, R30 independently of one another H, ($C_1$–$C_6$)-alkyl.

A a group of the formula —(C(R31)(R32))$_m$—, in which one member may be replaced by an element from the group of O, N(R33);

preferably a bond or a group of the formula —(C(R31)(R32))$_m$— in which one member is replaced by an element from the group of O, N(R33);

particularly preferably a bond, or a group of the formula (C(R31)(R32))$_m$— in which one member is replaced by an element from the group of O, N(R33), and the group bonds via the heteroatom in position 4 (relative to the cyclic urea) on the cyclohexane ring of the formula I;

m 0, 1, 2, 3;
preferably 0, 1, 3;

R31, R32, R33 independently of one another H, ($C_1$–$C_6$)-alkyl, aryl.

If radicals or substituents may occur more than once in the compounds of the formula I, such as, for example, R2, they may all, independently of one another, have the indicated meanings and be identical or different.

The invention relates to compounds of the formula I in the form of their racemates, enantiomer-enriched mixtures and pure enantiomers, and to their diastereomers and mixtures thereof.

The alkyl, alkenyl and alkynyl radicals in the substituents R1, R2, R3, R4, R5, R6, R7, R8, R9, R10, R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42, R43, R44, R45, R46, R46, R47, R48, R49, R50, R51, R52, R53, R54, R55, R56, R57, R58 and R59 may be either straight-chain, branched or optionally halogenated.

In a further embodiment, the alkyl, alkenyl and alkynyl radicals in the substituents R1, R2, R3, R4, R5, R6, R7, R8, R9, R10, R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42, R43, R44, R45, R46, R47, R48, R49, R50, R51, R52, R53, R54, R55, R56, R57, R58 and R59 may be both straight-chain, branched and/or optionally substituted by substituents such as aryl, heteroaryl, alkoxy or halogen. This also applies if the alkyl, alkenyl and alkynyl radicals are part of another group, for example part of an alkoxy group (such as ($C_1$–$C_4$)-alkoxy-($C_1$–$C_4$)-alkyl)). Suitable halogens are fluorine, chlorine, bromine and iodine, preferably fluorine, chlorine and bromine, particularly preferably fluorine.

Examples of alkyl groups are: methyl, ethyl, propyl, butyl, pentyl, hexyl, heptyl and octyl. Included therein are both the n isomers of these radicals and branched isomers such as isopropyl, isobutyl, isopentyl, sec-butyl, tert-butyl, neopentyl, 3,3-dimethylbutyl etc. Unless described otherwise, the term alkyl additionally includes alkyl radicals which are unsubstituted or optionally substituted by one or more further radicals, for example 1, 2, 3 or 4 identical or different radicals such as aryl, heteroaryl, alkoxy or halogen. It is moreover possible for the additional substituents to occur in any position of the alkyl radical.

Cycloalkyl means for the purposes of the present application cycloalkyl and cycloalkyl-alkyl (alkyl which is substituted in turn by cycloalkyl, e.g. cyclopropylmethyl), where cycloalkyl has at least 3 carbon atoms. Examples of cycloalkyl radicals are: cyclopropyl, cyclobutyl, cyclopentyl, cyclohexyl, cycloheptyl, cyclooctyl, cyclononyl and cyclodecyl. Optional possibilities are also polycyclic ring systems such as decalinyl, norbornanyl, bornanyl or adamantanyl. The cycloalkyl radicals may be unsubstituted or optionally substituted by one or more further radicals as listed above by way of example for the alkyl radicals.

Examples of alkenyl and alkynyl groups are: vinyl, 1-propenyl, 2-propenyl (allyl), 2-butenyl, 2-methyl-2-propenyl, 3-methyl-2-butenyl, ethynyl, 1-propynyl, 2-propynyl (propargyl), 1-butynyl, 2-butynyl or 3-butynyl.

Cycloalkenyl means for the purposes of the present application cycloalkenyl radicals and cycloalkenyl-alkyl radicals (alkyl which is substituted by cycloalkenyl), which comprise at least three carbon atoms. Examples of cycloalkenyl are: cyclopentenyl, cyclohexenyl, cycloheptenyl and cyclooctenyl.

The alkenyl radicals and cycloalkenyl radicals may have one to three conjugated or unconjugated double bonds (thus also alk-dienyl and alk-trienyl radicals), preferably one double bond in a straight or branched chain. The same applies to the triple bonds in alkynyl radicals. The alkenyl and alkynyl radicals may be unsubstituted or optionally substituted by one or more further radicals as listed above by way of example for the alkyl radicals.

Aryl refers in the present invention to radicals derived from monocyclic or bicyclic aromatic compounds comprising no ring heteroatoms. Where aryl refers to systems which are not monocyclic, the saturated form (perhydroform) or the partially unsaturated from (for example the dihydroform or tetrahydroform) is also possible, where the respective forms are known and stable, for the second ring. The term aryl also includes in the present invention for example bicyclic radicals in which both rings are aromatic and bicyclic radicals in which only one ring is aromatic. Examples of aryl are: phenyl, naphthyl, indanyl, 1,2-dihydronaphthenyl, 1,4-dihydronaphthenyl, indenyl or 1,2,3,4-tetrahydronaphthyl. Aryl is particularly preferably phenyl or naphthyl. The term "aryl" thus means in particular a phenyl or naphthyl group.

Heteroaryl radicals mean radicals derived from monocyclic or bicyclic aromatic compounds comprising ring heteroatoms, preferably N, O or S. Otherwise, the statements made about aryl radicals apply to heteroaryl radicals.

The aryl and heteroaryl radicals may be unsubstituted or substituted by one or more further radicals. Suitable further radicals are listed by way of example above for the alkyl radicals.

The compounds of the formula I may comprise one or more centers of asymmetry. The compounds of the formula I may therefore be in the form of their racemates, enantiomer-enriched mixtures, pure enantiomers, diastereomers and diastereomer mixtures. The present invention includes all these isomeric forms of the compounds of the formula I. These isomeric forms can be obtained by known methods even if not expressly described in some cases.

Mono-, bi- or spirocyclic rings may be saturated, partially saturated or unsaturated and also bridged.

C═C means a group of the formula R'C═CR" in which R' and R" are independently of one another H, $(C_1-C_8)$-alkyl, preferably H.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric, sulfonic and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, trifluoromethanesulfonic, succinic, p-toluenesulfonic, tartaric and trifluoroacetic acid. For medical purposes the chlorine salt is particularly preferably used. Suitable pharmaceutically acceptable basic salts are ammonium salts, alkali metal salts (such as sodium and potassium salts), alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention, as described, for example, in H. Okada et al., Chem. Pharm. Bull. 1994, 42, 57–61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula (I)" hereinafter refer to compound(s) of the formula (I) as described above, and their salts, solvates and physiologically functional derivatives as described herein.

If radicals or substituents may occur more than once in the compounds of the formula I, they may all, independently of one another, have the indicated meanings and be identical or different.

In a further preferred embodiment, the meanings for the radicals R1, R2, the index n and the groups K, E, X, D, G, A and Q are as follows:

R1 $(C_1-C_8)$-alkyl, $(C_1-C_4)$-alkoxy-$(C_1-C_4)$-alkyl, a 3 to 10-membered mono-, bi- or spirocyclic ring which may include 0 to 3 heteroatoms selected from the group of oxygen, nitrogen and sulfur, where the ring system may be additionally substituted by F, Cl, Br, $CF_3$, CN, $(C_1-C_6)$-alkyl, O—$(C_1-C_8)$-alkyl, $(C_0-C_2)$-alkylene-aryl, oxo, CO(R3), CON(R4)(R5), hydroxy, N(R7)CO $(C_1-C_6)$-alkyl, N(R8)(R9) or $SO_2CH_3$;

preferably $(C_1-C_8)$-alkyl, $(C_1-C_4)$-alkoxy-$(C_1-C_4)$-alkyl, a 3 to 10-membered mono- or bicyclic ring which may include 0 to 2 heteroatoms selected from the group of oxygen, nitrogen and sulfur, where the ring system may be additionally substituted by F, Cl, Br, $CF_3$, CN, $(C_1-C_6)$-alkyl, O—$(C_1-C_8)$-alkyl, oxo, CO(R3), CON (R4)(R5), N(R7)CO$(C_1-C_6)$-alkyl, or $SO_2CH_3$;

R3, R4, R5, R7, R8, R9 independently of one another H, $(C_1-C_8)$-alkyl;

K a bond, $OCH_2$, $CH_2O$, $(C(R10)(R11))_z$, C≡C;

z 1, 2, 3, 4; preferably 1, 2, 3; particularly preferably 1,2;

R10, R11 independently of one another H, $(C_1-C_8)$-alkyl;

E 3–8 membered bivalent carbo- or heterocyclic ring structure having 0–4 heteroatoms from the group of N, O and S, which may optionally have substituents from the group of H, F, Cl, Br, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, O—$(C_3-C_8)$cycloalkyl, $(C_3-C_8)$cycloalkenyl, $(C_2-C_6)$-alkynyl, ($C_0$–$C_8$)-alkylene-aryl, O—($C_0$–$C_8$)-alkylene-aryl, S-aryl, N(R12)(R13), $SO_2$—$CH_3$, N(R16)CO(R17), N(R18)$SO_2$(R19), CO(R20) and be mono- or bicyclic; preferably 5–7 membered bivalent carbo- or heterocyclic ring structure having 0–3 heteroatoms from the group of N, O and S, which may optionally have substituents from the group of H, F, Cl, Br, OH, $CF_3$, $NO_2$, CN, $OCF_3$, O—($C_1$–$C_6$)-alkyl, S—($C_1$–$C_6$)-alkyl, ($C_1$–$C_6$)-alkyl, ($C_2$–$C_6$)-alkenyl, O—($C_0$–$C_8$)-alkylene-aryl, S-aryl, N(R12)(R13), $SO_2$—$CH_3$, N(R16)CO(R17), CO(R20) and be mono- or bicyclic; particularly preferably 5–7 membered bivalent carbo- or heterocyclic ring structure having 0–2 heteroatoms from the group of N, O and S, which may optionally have substituents from the group of H, F, Cl, Br, OH, $CF_3$, $NO_2$, $OCF_3$, O—($C_1$–$C_6$)-alkyl, ($C_1$–$C_6$)-alkyl, ($C_2$–$C_6$)-alkenyl, N(R12)(R13), $SO_2$—$CH_3$, CO(R20), e.g. E is selected from the group consisting of

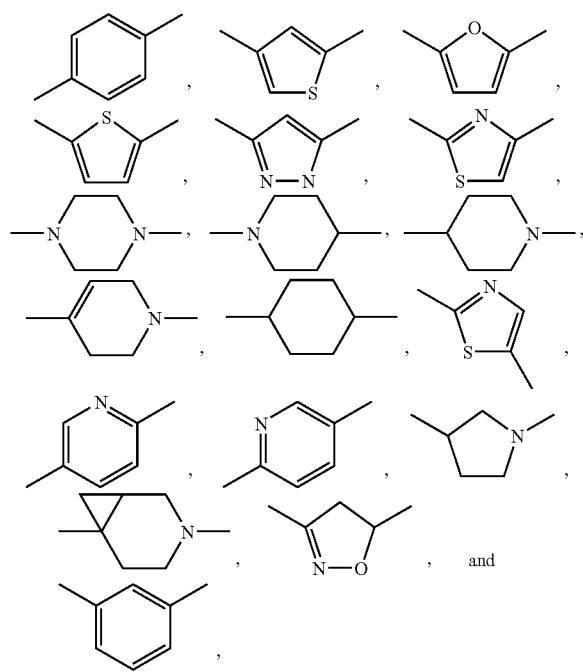

which may optionally have substituents from the group of H, F, Cl, Br, OH, $CF_3$, $NO_2$, $OCF_3$, O—($C_1$–$C_6$)-alkyl, ($C_1$–$C_6$)-alkyl, ($C_2$–$C_6$)-alkenyl, N(R12)(R13), CO(R20), preferably H, F, Cl, Br, O—($C_1$–$C_6$)-alkyl, ($C_1$–$C_6$)-alkyl, CO(R20);

preferably

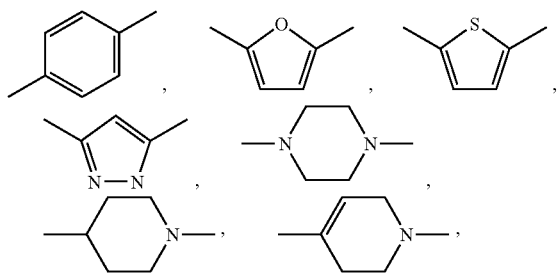

-continued

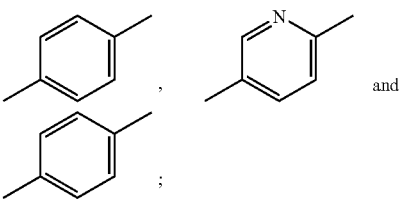

which may optionally have the aforementioned substituents;

particularly preferably

R12, R13, R16, R18 independently of one another H, ($C_1$–$C_8$)-alkyl;

R17, R19, R20 independently of one another H, ($C_1$–$C_8$)-alkyl, aryl; preferably independently of one another H, ($C_1$–$C_8$)-alkyl;

X a bond, —$CH_2$—$CH_2$—; preferably a bond;

D, G either D is N and G is CH or D is CH and G is N or D and G are both CH; D and G are preferably both CH;

R2 OH, O—($C_1$–$C_6$)-alkyl, O—($C_1$–$C_4$)-alkoxy-($C_1$–$C_4$)-alkyl, ($C_1$–$C_6$)-alkyl; preferably O—($C_1$–$C_6$)-alkyl, ($C_1$–$C_6$)-alkyl;

n 0, 1, 2; preferably 0 or 1;

Q N(R24)(R25), a 3 to 8-membered monocyclic ring which may include 0 to 3 heteroatoms selected from the group of oxygen, nitrogen and sulfur, where the ring system may be additionally substituted by N(R24)(R25), F, Cl, Br, $CF_3$, $NO_2$, CN, ($C_1$–$C_6$)-alkyl, O—($C_1$–$C_8$)-alkyl, ($C_1$–$C_4$)-alkoxy-($C_1$–$C_4$)-alkyl, ($C_0$–$C_8$)-alkylene-aryl, oxo, CO(R26), CON(R27)(R28), hydroxy, hydroxy-($C_1$–$C_4$)-alkyl, COO(R29), N(R30)CO($C_1$–$C_6$)-alkyl or $SO_2CH_3$, preferably N(R24)(R25), F, Cl, ($C_1$–$C_6$)-alkyl, O—($C_1$–$C_8$)-alkyl, ($C_1$–$C_4$)-alkoxy-($C_1$–$C_4$)-alkyl, ($C_0$–$C_8$)-alkylene-aryl, oxo, CO(R26), N(R30)CO ($C_1$–$C_6$)-alkyl or $SO_2CH_3$;

R26, R27, R28, R29, R30 independently of one another H, ($C_1$–$C_6$)-alkyl; preferably ($C_1$–$C_6$)-alkyl;

A a group of the formula —(C(R31)(R32))$_m$— in which 0–2 members may be replaced by an element from the group of O, N(R33), CO; preferably a group of the formula —(C(R31)(R32))$_m$— in which 1 member may be replaced by an element from the group of O, N(R33);

m 0, 1, 2, 3, 4; preferably 0, 1, 3 or 4;

R31, R32, R33 independently of one another H, ($C_1$–$C_6$)-alkyl, aryl; preferably H;

R24, R25 independently of one another H, ($C_1$–$C_8$)-alkyl, —($CH_2$)$_o$—R36, CO—($C_1$–$C_8$)-alkyl, or R24 and R25 form together with the nitrogen atom to which they are bonded a 4 to 10-membered, mono-, bi- or spirocyclic ring which, apart from the nitrogen atom, may include 0 to 2 additional heteroatoms selected from the group of oxygen, nitrogen and sulfur, where the heterocyclic ring system may additionally be substituted by F, Cl, ($C_1$–$C_6$)- alkyl, O—($C_1$–$C_8$)-alkyl, oxo, CO(R44), CON(R45)(R46), hydroxy, N(R48)CO($C_1$–$C_6$)-alkyl or N(R49)(R50), preferably F, ($C_1$–$C_6$)-alkyl, O—($C_1$–$C_8$)-alkyl, oxo, CO(R44), N(R48)CO($C_1$–$C_6$)-alkyl or N(R49)(R50);

o 0, 1, 2, 3, 4;

R36 OH, 5–10 membered mono- or bicyclic ring which may comprise one or more heteroatoms from the group of N, O and S, and the 5–10 membered ring may comprise further substituents such as F, Cl, Br, OH, $CF_3$, oxo, O—($C_1$–$C_6$)-alkyl, ($C_1$–$C_6$)-alkyl, O—($C_0$–$C_2$)-alkylene-aryl, ($C_0$–$C_2$)-alkylene-aryl and N(R55)(R56); preferably a 5–8 membered monocyclic ring which may comprise 0–2 heteroatoms from the group of N, O and S, and the 5–8 membered ring may comprise further substituents such as F, oxo, O—($C_1$–$C_6$)-alkyl, ($C_1$–$C_6$)-alkyl, ($C_0$–$C_2$)-alkylene-aryl and N(R55)(R56);

R44, R45, R46, R48, R49, R50 independently of one another H, ($C_1$–$C_6$)-alkyl;

R55, R56 independently of one another H, ($C_1$–$C_8$)-alkyl.

It is very particularly preferred for D and G in the aforementioned compounds of the formula I each to be CH.

In a further preferred embodiment, the present invention relates to compounds of the formula I in which the substituents of the cyclohexylene group are in para position relative to one another, i.e. the compounds of the formula I have the following structure Ia:

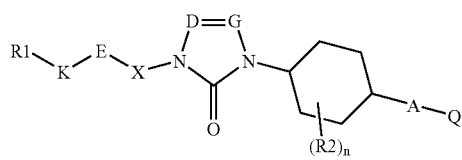

Ia where the radicals R1 and R2, the index n and the groups K, E, X, D, G, A and Q have the aforementioned meanings.

In addition, very particularly preferred compounds of the formula I are those in which the group Q comprises at least one nitrogen atom, where the nitrogen atom may be present in ring Q and/or in a substituent of ring Q.

Particularly preferred compounds of the formula I are those in which the group A-Q has one of the following meanings:

if:

A is a group of the formula —(C(R31)(R32))$_m$— in which 0–2 members may be replaced by an element from the group of O, N(R33), CO; preferably a group of the formula —(C(R31)(R32))$_m$— in which 1 member may be replaced by an element from the group of O, N(R33);

where m is 1, 2, 3, 4; preferably 1, 3 or 4;

and

R31, R32, R33 are independently of one another H, ($C_1$–$C_6$)-alkyl, aryl; preferably H;

then

Q is N(R24)(R25);

where

R24, R25 are independently of one another H, ($C_1$–$C_8$)-alkyl, —(CH$_2$)$_o$—R36, CO—($C_1$–$C_8$)-alkyl, or R24 and R25 form together with the nitrogen atom to which they are bonded a 4 to 10-membered mono-, bi- or spirocyclic ring which, apart from the nitrogen atom, may include 0 to 2 additional heteroatoms selected from the group of oxygen, nitrogen and sulfur, where the heterocyclic ring system may additionally be substituted by F, Cl, ($C_1$–$C_6$)-alkyl, O—($C_1$–$C_8$)-alkyl, oxo, CO(R44), CON(R45)(R46), hydroxy, N(R48)CO($C_1$–$C_6$)-alkyl or N(R49)(R50), preferably F, ($C_1$–$C_6$)-alkyl, O—($C_1$–$C_8$)-alkyl, oxo, CO(R44), N(R48)CO($C_1$–$C_6$)-alkyl or N(R49)(R50);

o is 0, 1, 2, 3, 4;

R36 is OH, 5–10 membered mono- or bicyclic ring which may comprise one or more heteroatoms from the group of N, O and S, and the 5–10 membered ring may comprise further substituents such as F, Cl, Br, OH, $CF_3$, oxo, O—($C_1$–$C_6$)-alkyl, ($C_1$–$C_6$)-alkyl, O—($C_0$–$C_2$)-alkylene-aryl, ($C_0$–$C_2$)-alkylene-aryl and N(R55)(R56), preferably a 5–8 membered monocyclic ring which may comprise 0–2 heteroatoms from the group of N, O and S, and the 5–8 membered ring may comprise further substituents such as F, oxo, O—($C_1$–$C_6$)-alkyl, ($C_1$–$C_6$)-alkyl, ($C_0$–$C_2$)-alkylene-aryl and N(R55)(R56);

R44, R45, R46, R48, R49, R50 are independently of one another H, ($C_1$–$C_6$)-alkyl;

and

R55, R56 are independently of one another H, ($C_1$–$C_8$)-alkyl;

if:

A is a group of the formula —(C(R31)(R32))$_m$— in which 0–2 members may be replaced by an element from the group of O, N(R33), CO; preferably a group of the formula —(C(R31)(R32))$_m$— in which 1 member may be replaced by an element from the group of O, N(R33);

where m is 0, 1, 2, 3, 4; preferably 0 or 1;

and

R31, R32, R33 are independently of one another H, ($C_1$–$C_6$)-alkyl, aryl; preferably H;

where A very particularly preferably is a bond or N(R33);

then

Q is a 3 to 8-membered monocyclic ring which may include 0 to 3 heteroatoms selected from the group of oxygen, nitrogen and sulfur, where the ring system may additionally be substituted by F, Cl, Br, $CF_3$, $NO_2$, CN; ($C_1$–$C_6$)-alkyl, O—($C_1$–$C_8$)-alkyl, ($C_1$–$C_4$)-alkoxy-($C_1$–$C_4$)-alkyl, ($C_0$–$C_8$)-alkylene-aryl, oxo, CO(R26), CON(R27)(R28), hydroxy, hydroxy-($C_1$–$C_4$)-alkyl, COO(R29), N(R30)CO($C_1$–$C_6$)-alkyl or $SO_2CH_3$; preferably a 5 to 7-membered monocyclic ring which comprises one or two nitrogen atoms, where the ring system may additionally be substituted by ($C_1$–$C_6$)-alkyl, ($C_1$–$C_4$)-alkoxy-($C_1$–$C_4$)-alkyl or ($C_0$–$C_2$)-alkylene-aryl;

where

R26, R27, R28, R29, R30 are independently of one another H, ($C_1$–$C_6$)-alkyl; preferably ($C_1$–$C_6$)-alkyl;

if:

A is a group of the formula —(C(R31)(R32))$_m$— in which 0–2 members may be replaced by an element from the group of O, N(R33), CO; preferably a group of the formula —(C(R31)(R32))$_m$— in which 1 member may be replaced by an element from the group of O, N(R33);

where m is 0, 1, 2, 3, 4; preferably o or 1;

and

R31, R32, R33 are independently of one another H, $(C_1–C_6)$-alkyl, aryl; preferably H;

where A very particularly preferably is a bond or N(R33);

then

Q is a 3 to 8-membered monocyclic ring which may include 0 to 3 heteroatoms selected from the group of oxygen, nitrogen and sulfur, where the ring system is additionally substituted by N(R24)(R25) and may additionally be substituted by F, Cl, Br, $CF_3$, $NO_2$, CN, $(C_1–C_6)$-alkyl, O—$(C_1–C_8)$-alkyl, $(C_1–C_4)$-alkoxy-$(C_1–C_4)$-alkyl, $(C_0–C_8)$-alkylene-aryl, oxo, CO(R26), CON(R27)(R28), hydroxy, hydroxy-$(C_1–C_4)$-alkyl, COO(R29), N(R30)CO $(C_1–C_6)$-alkyl or $SO_2CH_3$; preferably a 3 to 8-membered monocyclic ring which may include 0 to 1 heteroatom selected from the group of oxygen, nitrogen and sulfur, where the ring system is additionally substituted by N(R24)(R25) and may additionally be substituted by F, Cl, Br, $CF_3$, $NO_2$, CN, $(C_1–C_6)$-alkyl, O—$(C_1–C_8)$-alkyl, $(C_1–C_4)$-alkoxy-$(C_1–C_4)$-alkyl, $(C_0–C_8)$-alkylene-aryl, oxo, CO(R26), CON(R27)(R28), hydroxy, hydroxy-$(C_1–C_4)$-alkyl, COO(R29), N(R30)CO$(C_1–C_6)$-alkyl or $SO_2CH_3$, preferably F, $(C_1–C_6)$-alkyl, O—$(C_1–C_8)$-alkyl, $(C_1–C_4)$-alkoxy-$(C_1–C_4)$-alkyl, $(C_0–C_8)$-alkylene-aryl, oxo, CO(R26), N(R30)CO$(C_1–C_6)$-alkyl or $SO_2CH_3$;

where

R26, R27, R28, R29, R30 are independently of one another H, $(C_1–C_6)$-alkyl; preferably $(C_1–C_6)$-alkyl;

and

R24, R25 are independently of one another H, $(C_1–C_8)$-alkyl, —$(CH_2)_o$—R36, CO—$(C_1–C_8)$-alkyl, or R24 and R25 form together with the nitrogen atom to which they are bonded a 4 to 10-membered mono-, bi- or spirocyclic ring which, apart from the nitrogen atom, may include 0 to 2 additional heteroatoms selected from the group of oxygen, nitrogen and sulfur, where the heterocyclic ring system may additionally be substituted by F, Cl, $(C_0–C_6)$-alkyl, O—$(C_1–C_8)$-alkyl, oxo, CO(R44), CON(R45)(R46), hydroxy, N(R48)CO$(C_1–C_6)$-alkyl or N(R49)(R50), preferably F, $(C_1–C_6)$-alkyl, O—$(C_1–C_8)$-alkyl, oxo, CO(R44), N(R48)CO$(C_1–C_6)$-alkyl or N(R49)(R50);

o is 0, 1, 2, 3, 4;

R36 is OH, 5–10 membered mono- or bicyclic ring which may comprise one or more heteroatoms from the group of N, O and S and the 5–10 membered ring may comprise further substituents such as F, Cl, Br, OH, $CF_3$, oxo, O—$(C_1–C_6)$-alkyl, $(C_1–C_6)$-alkyl, O—$(C_0–C_2)$-alkylene-aryl, $(C_0–C_2)$-alkylene-aryl and N(R55)(R56), preferably a 5–8 membered monocyclic ring which may comprise 0–2 heteroatoms from the group of N, O and S, and the 5–8 membered ring may comprise further substituents such as F, oxo, O—$(C_1–C_6)$-alkyl, $(C_1–C_6)$-alkyl, $(C_0–C_2)$-alkylene-aryl and N(R55)(R56);

R44, R45, R46, R48, R49, R50 are independently of one another H, $(C_1–C_6)$-alkyl;

and

R55, R56 are independently of one another H, $(C_1–C_8)$-alkyl.

Examples of particularly preferred A–Q groups are listed below:

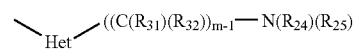

in which Het is O, S, N(R33), preferably O, N(R33), and m is 3 or 4

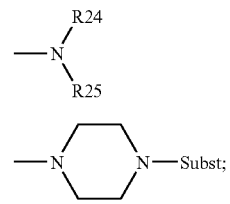 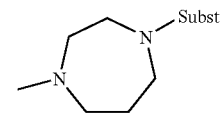

in which Subst is H, $(C_1–C_6)$-alkyl, hydroxy-$C_1–C_4$-alkyl, preferably H, $(C_1–C_6)$-alkyl

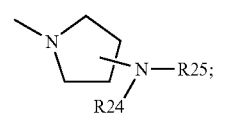 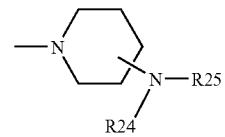

in which the radicals R24, R25, R31, R32 and R33 have the aforementioned meanings.

In a further particularly preferred embodiment, the present invention relates to compounds of the formula Iaa

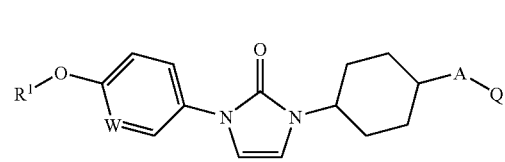

in which
W is CH or N, and the radical R1 and the groups A and Q have the aforementioned meanings.

The compounds of the invention of the formula I can be prepared for example by processes analogous to the preparation processes disclosed in WO 03/057220, for example by cyclization and/or coupling reactions. Suitable starting substances can be prepared by processes known to the skilled worker, and some are commercially available.

In a preferred embodiment, the compounds of the formula I are prepared by a process including the following steps:

a) preparation of a compound of the formula II: the basic structure (1,4-dioxaspiro[4.5]decan-8-one) is commercially available. Substituted variants can be prepared by processes known from the literature (see, for example, Nakamura, M. et al.; J. Am. Chem. Soc. 2003, 125(21), 6362–6363; Kawafuchi, H. et al.; Tetrahedron Lett. 2002, 43(11), 2051–2054; Beauhaire, J. et al.; Tetrahedron Lett. 1995, 36(7), 1043–1046)

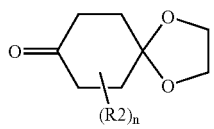

b) reaction of the compound of the formula II with

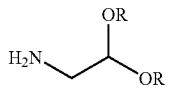

under reductive amination conditions, where R=lower alkyl, preferably ethyl or methyl, to give a compound of the formula III

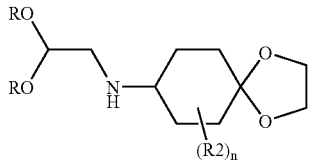

c) coupling of the compound of the formula III with phosgene (or a known phosgene equivalent, for example carbonyldiimidazole) and a primary amine of the formula

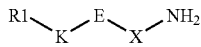

and subsequent deprotection of the acetals, with simultaneous cyclization resulting in a compound of the formula IV

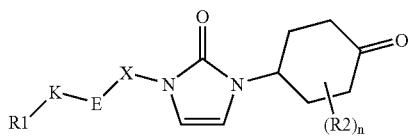

d) reaction with a primary or secondary amine under reductive amination conditions, resulting in compounds of the formula I whose A–Q group is linked via a nitrogen atom to the cyclohexylene ring

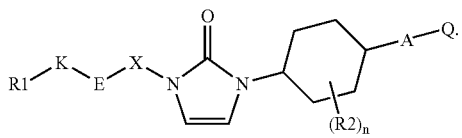

Further compounds of the invention of the formula I can be obtained by analogous processes, the skilled worker being aware how the process described above must be altered in order to obtain further compounds of the formula I.

Suitable reaction conditions and reagents for carrying out steps a) to d) of the process of the invention are known to the skilled worker.

Two preparation routes for compounds of the formula I are indicated by way of example below:

Exemplary route 1

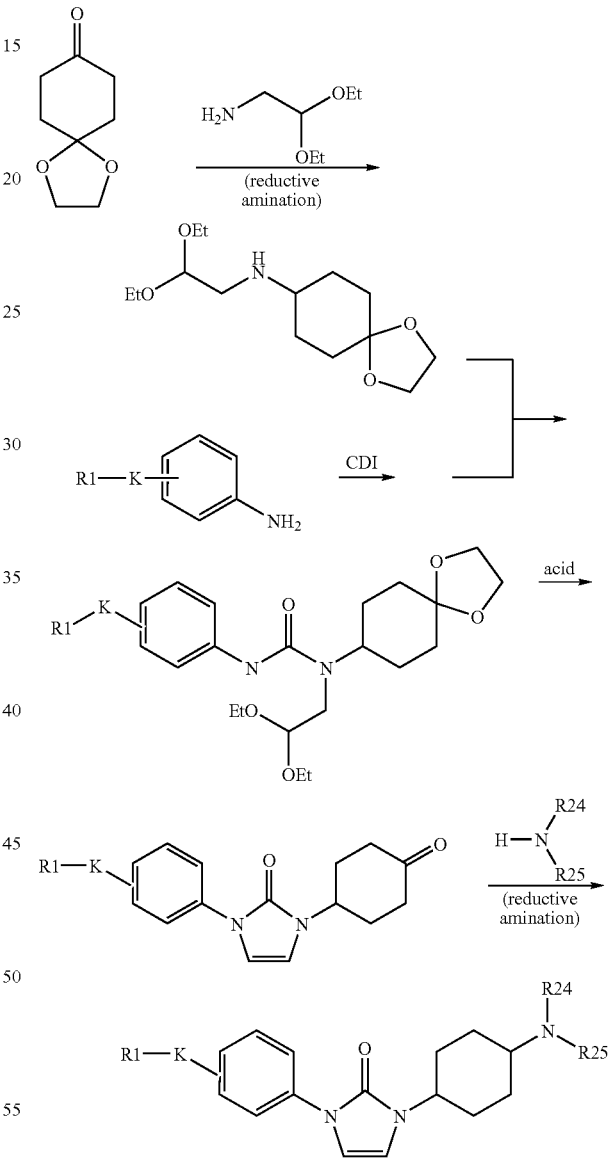

Exemplary route 2

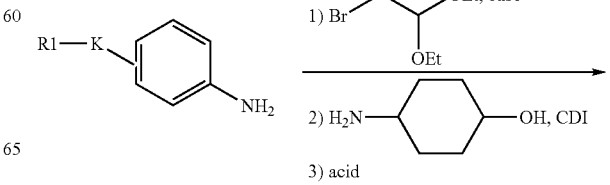

-continued

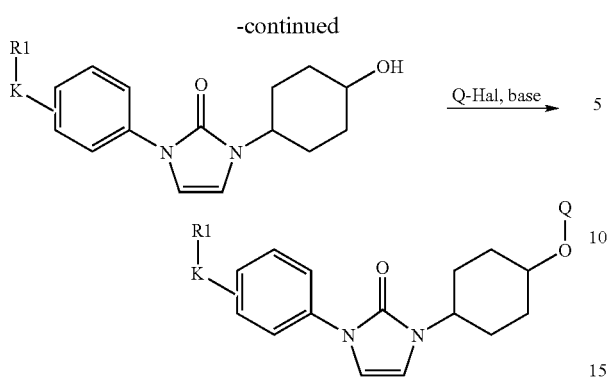

In exemplary routes 1 and 2, R1, K and Q have the aforementioned meanings.

Use

This invention further relates to the use of compounds of the formula I and their pharmaceutical compositions as MCH receptor ligands. The MCH receptor ligands of the invention are particularly suitable as modulators of the activity of the MCH1R.

The role of MCH in regulating the energy balance has now been well documented (Qu, D. et al.; Nature 1996, 380, 243–7; Shimada, M. et al. Nature 1998, 396, 670–4; Chen, Y et al. Endocrinology 2002, 143, 2469–77; Endocrinology 2003, 144, 4831–40; Review: G. Hervieu, Expert Opin. Ther. Targets 2003, 7, 495–511).

There are also indications that MCH antagonists can have a beneficial influence on centrally related disorders such as, for example, depression (Borowsky, B. et al.; Nature Medicine 2002, 8, 825–30; Review: G. Hervieu, Expert Opin. Ther. Targets 2003, 7, 495–511).

Compounds of this type are particularly suitable for the treatment and/or prevention of
1. Obesity
2. Diabetes mellitus, especially type 2 diabetes, including the prevention of the sequelae associated therewith.
Particular aspects in this connection are
hyperglycemia,
improvement in insulin resistance,
improvement in glucose tolerance,
protection of the pancreatic β cells
prevention of macro- and microvascular disorders
3. Dyslipidemias and their sequelae such as, for example, atherosclerosis, coronary heart disease, cerebrovascular disorders etc, especially those (but not restricted thereto) which are characterized by one or more of the following factors:
high plasma triglyceride concentrations, high postprandial plasma triglyceride concentrations,
low HDL cholesterol concentration
4. Various other conditions which may be associated with the metabolic syndrome, such as:
thromboses, hypercoagulable and prothrombotic stages (arterial and venous)
high blood pressure
heart failure such as, for example (but not restricted thereto), following myocardial infarction, hypertensive heart disease or cardiomyopathy
5. Psychiatric indications such as
depressions
anxiety states
disturbances of the circadian rhythm
affection disorders
schizophrenia
addictive disorders Formulations The amount of a compound of formula (I) necessary to achieve the desired biological effect depends on a number of factors, for example the specific compound chosen, the intended use, the mode of administration and the clinical condition of the patient. The daily dose is generally in the range from 0.001 mg to 100 mg, preferably 0.3 mg to 100 mg (typically from 0.01 mg to 50 mg, preferably 3 mg to 50 mg) per day and per kilogram of bodyweight, for example 0.1–10 mg/kg/day, preferably 3–10 mg/kg.day. An intravenous dose may be, for example, in the range from 0.001 mg to 1.0 mg/kg, preferably 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 0.05 to 1000 mg, typically from 0.5 to 600 mg, or in a further embodiment from 1.0 to 1000 mg, typically from 10 to 600 mg. In the case of pharmaceutically acceptable salts, the aforementioned weight data are based on the weight of the free compound from which the salt is derived. For the prophylaxis and therapy of the abovementioned conditions, the compounds of formula (I) may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula (I). The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula (I) used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula (I) with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula (I), which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula (I) with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by beneficial effects on lipid metabolism, and they are particularly suitable for weight reduction and for maintaining a reduced weight after weight reduction has taken place in mammals and as anorectic agents. The compounds are distinguished by their low toxicity and their few side effects. The compounds can be employed alone or in combination with other weight-reducing or anorectic active ingredients. Further anorectic active ingredients of this type are mentioned, for example, in the Rote Liste, chapter 01 under weight-reducing agents/appetite suppressants, and they also include active ingredients which increase the energy turnover of the organism and thus lead to weight reduction or else those which influence the general metabolism of the organism in such a way that an increased calorie intake does not lead to an enlargement of the fat depots and a normal calorie intake leads to a reduction of the fat depots of the organism. The compounds are suitable for the prophylaxis and, in particular, for the treatment of excessive weight or obesity. The compounds are further suitable for the prophylaxis and, in particular, for the treatment of type II diabetes, of arteriosclerosis and for normalizing lipid metabolism and for the treatment of high blood pressure.

Combinations with Other Medicaments

In a further aspect of the invention the compounds of the formula I can be administered alone or in combination with one or more further pharmacologically active substances which have, for example, favorable effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Further particularly suitable pharmacologically active substances are:

Antidiabetics

All antidiabetics disclosed for example in the Rote Liste 2001, chapter 12. They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Suitable antidiabetics include all insulins and insulin derivatives, such as, for example, Lantus® or HMR 1964 or Apidra®, and other fast-acting insulins (see, for example U.S. Pat. No. 6,221,633), amylin, GLP-1 and GLP-2 derivatives, as described in WO 01/04146 or else such as those disclosed in WO 98/08871 of Novo Nordisk A/S, and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon-receptor-antagonists, GLP-1 agonists, DPP-IV inhibitors, potassium channel openers such as, for example, those disclosed in WO 97/26265 and WO 99/03861 of Novo Nordisk A/S, insulin sensitizers, activators of the insulin receptor kinase GSK3-beta inhibitors, inhibitors of liver enzymes involved in the stimulation of gluconeogenesis and/or glycogenolysis, for example inhibitors of glycogen phosphorylase, modulators of glucose uptake and glucose excretion, compounds which alter lipid metabolism and lead to a change in the blood lipid composition, such as antihyperlipidemic active ingredients and antilipidemic active ingredients, e.g. HMGLoA reductase inhibitors, inhibitors of cholesterol transport/of cholesterol uptake, inhibitors of bile acid reabsorption or inhibitors of microsomal triglyceride transfer protein (MTP), compounds which reduce food intake and/or food absorption, PPAR and RXR agonists and active ingredients which act on the ATP-dependent potassium channel of the beta cells. In one embodiment of the invention, the present compounds are administered in combination with insulin.

In one embodiment of the invention, the compounds of the formula I are administered in combination with substances which influence hepatic glucose production such as, for example, glycogen phosphorylase inhibitors (see: WO 01/94300, WO 02/096864, WO 03/084923, WO 03/084922, WO 03/104188).

In one embodiment, the compounds of the formula I are administered in combination with a sulfonylurea such as, for example, tolbutamide, glibenclamide, glipizide or glimepiride.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with a biguanide such as, for example, metformin.

In a further embodiment, the compounds of the formula I are administered in combination with a meglitinide such as, for example, repaglinide.

In one embodiment, the compounds of the formula I are administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with a DPPIV inhibitor as described, for example, in WO98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-β-hydroxyadamant-1-ylamino)acetyl]pyrrolidine-2-(S)-carbonitrile), TS021 ((2S, 4S)-4-fluoro-1-[[(2-hydroxy-1,1-dimethylethyl)amino]-acetyl]pyrrolidine-2-carbonitrile monobenzenesulfonate).

In one embodiment of the invention, the compounds of the formula I are administered in combination with a PPAR-gamma agonist such as, for example, rosiglitazone, pioglitazone.

In one embodiment, the compounds of the formula I are administered in combination with compounds with an inhibitory effect on SGLT-1 and/or 2, as disclosed directly or indirectly for example in PCT/EP03/06841, PCT/EP03/13454 and PCT/EP03/13455.

In one embodiment, the compounds of the formula I are administered in combination with an α-glucosidase inhibitor such as, for example, miglitol or acarbose.

In one embodiment, the compounds of the formula I are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid reabsorption inhibitor (see, for example, U.S. Pat. No. 6,245,744, U.S. Pat. No. 6,221,897, U.S. Pat. No. 6,277,831, EP 0683 773, EP 0683 774).

In one embodiment of the invention, the compounds of the formula I are administered in combination with a polymeric bile acid adsorbent such as, for example, cholestyramine or colesevelam.

In one embodiment of the invention, the compounds of the formula I are administered in combination with a cholesterol absorption inhibitor as described for example in WO 0250027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September–October), 18(5), 230–6.) Caromax is a carob-containing product from Nutrinova, Nutrition Specialties & Food Ingredients GmbH, Industriepark Hoechst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP-citrate lyase inhibitor.

In one embodiment of the invention, the compounds of the formula I are administered in combination with a squalene synthetase inhibitor.

In one embodiment of the invention, the compounds of the formula I are administered in combination with a lipoprotein(a) antagonist.

Antiobesity Agents

In one embodiment of the invention, the compounds of the formula I are administered in combination with a lipase inhibitor such as, for example, orlistat.

In one embodiment, the further active ingredient is fenfluramine or dexfenfluramine.

In another embodiment, the further active ingredient is sibutramine. In another embodiment, the further active ingredient is rimonabant.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554–558), NPY antagonists, e.g. naphthalene-1-sulfonic acid {4-[(4-aminoquinazolin-2-ylamino)methyl]-cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea hydrochloride (SB-334867-A)), CBI antagonists/inverse agonists, H3 antagonists/inverse agonists (e.g. 3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), BRS3 agonists, galanin antagonists, ghrelin antagonists, MCH antagonists, mGluR5 antagonists, opioid antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), (NTF, CNTF derivatives (e.g. Axokine), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873–881), DA agonists (e.g. bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dexamphetamine, amphetamine, mazindole or phentermine.

In one embodiment, the compounds of the formula I are administered in combination with medicaments having effects on the coronary circulation and the vascular system, such as, for example, ACE inhibitors (e.g. ramipril), medicaments which act on the angiotensin-renine system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

In two articles which appeared simultaneously in Nature (Nature 400, 261–264, 1999; Nature 400, 265–269, 1999), two research groups separately described a highly specific receptor for melanin concentrating hormone (MCH). MCH assumes important functions in controlling food intake. Compounds which act on the MCH receptor therefore have an anorectic effect and are suitable for the treatment of obesity. Testing for an anorectic effect of the compounds of the invention of the formula I was therefore carried out as follows.

Functional measurements to determine IC50 values

Cloning of the cDNA for the human MCH receptor, preparation of a recombinant HEK293 cell line which expresses the human MCH receptor, and functional measurements with the recombinant cell line took place in analogy to the description by Audinot et al. (J. Biol. Chem. 276, 13554–13562, 2001). A difference from the reference was, however, the use of the plasmid pEAK8 from EDGE Biosystems (USA) for the construction of the expression vector. The host used for the transfection was a transformed HEK cell line named "PEAK Stable Cells" (likewise from EDGE Biosystems). Functional measurements of the cellular calcium flux after addition of agonist (MCH) in the presence of ligand of the invention took place with the aid of the FLIPR apparatus from Molecular Devices (USA), using protocols of the apparatus manufacturer.

Biological Activity Testing

The IC50 values measured for exemplary compounds 1, 2, 5 and 8 under the aforementioned conditions were of the order of 0.01 to 2 μM. Exemplary compounds 3, 6 and 9 showed IC50 values of from 2 to 10 μM.

The examples and preparation methods detailed below serve to illustrate the invention without, however, restricting it.

EXAMPLES

General Explanations a) Mode of Drawing the Structural Formulae

Only non-hydrogen atoms are depicted for clarity in the structural formulae of the examples given.

b) Salt Forms

Many of the compounds of the invention are bases and can form salts with appropriately strong acids. In particular, after purification of the compounds by HPLC chromatography using a trifluoroacetic acid-containing mobile phase they may be in the form of hydrotrifluoroacetates. These can be converted into the free bases shown by simple treatment of a solution of the salts for example with sodium carbonate solution.

c) Units of the Characterizing Data

The unit of the stated molecular weights is "g/mol". Peaks observed in the mass spectrum are indicated as integral quotient of the molar molecular ion mass and of the charge on the molecular ion (m/z).

Abbreviations

Unless indicated otherwise, the abbreviations in the examples hereinafter have the following meaning:
NaBH$_3$CN=sodium cyanoborohydride
DMF=N,N-dimethylformamide
EDC=1-(3-dimethylaminopropyl)-3-ethylcarbodiimide
THF=tetrahydrofuran
DMSO=dimethyl sulfoxide
HOBt=1-hydroxybenzotriazole
HOAt=1-hydroxy-7-azabenzotriazole
HCl=hydrochloric acid
HPLC=high performance liquid chromatography
PyBOP=benzotriazol-1-yloxytris(pyrrolidino)phosphonium hexafluorophosphate
CDI=carbonyldiimidazole

Example 1

(R)-N-(1-{4-[2-oxo-3-(4-phenoxyphenyl)-2,3-dihydroimidazol-1-yl]cyclohexyl}pyrrolidin-3-yl)acetamide

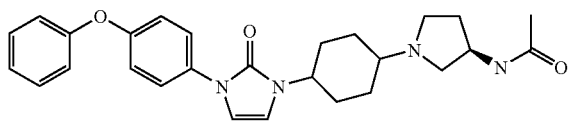

Method A

A mixture of 1-(4-oxocyclohexyl)-3-(4-phenoxyphenyl)-1,3-dihydroimidazol-2-one (348 mg), (R)-N-pyrrolidin-3-ylacetamide (128 mg) and dichloroethane (5 mL) was mixed with sodium triacetoxyborohydride (295 mg) and stirred for 48 hours. Sodium hydroxide solution (1 M) was added, and the mixture was extracted with ethyl acetate. The organic phase was dried over magnesium sulfate, filtered and concentrated. The residue was purified by preparative HPLC. The product with a molecular weight of 460.58 (C$_{27}$H$_{32}$N$_4$O$_3$) was obtained in this way; MS (ESI): 461 ([M+H]$^+$).

1-(4-oxocyclohexyl)-3-(4-phenoxyphenyl)-1,3-dihydroimidazol-2-one

Method B

A solution of 4-phenoxyaniline (2.0 g) in DMF (10 mL) was added to a solution of carbonyldiimidazole (1.8 g) in DMF (30 mL) at 0° C. After 30 minutes, (2,2-diethoxyethyl)-(1,4-dioxaspiro[4.5]dec-8-yl)amine (3.0 g) in DMF (10 mL) was added, and the mixture was heated at 80° C. for 30 minutes. Trifluoroacetic acid (5 mL) was added, and the mixture was kept at 80° C. for a further 5 hours. After cooling, the mixture was diluted with water and extracted with ethyl acetate. The organic phase was dried over magnesium sulfate, filtered and concentrated. The product with the molecular weight of 348.41 (C$_{21}$H$_{20}$N$_2$O$_3$) was obtained in this way; MS (ESI): 349 ([M+H]$^+$).

Analogously, 1-(4-cyclopentyloxyphenyl)-3-(4-oxocyclohexyl)-1,3-dihydroimidazol-2-one was obtained from 4-cyclopentyloxyaniline, 1-(6-cyclopentyloxypyridin-3-yl)-3-(4-oxocyclohexyl)-1,3-dihydroimidazol-2-one was obtained from 6-cyclopentyloxypyridin-3-ylamine and 1-(4-butoxyphenyl)-3-(4-oxocyclohexyl)-1,3-dihydroimidazol-2-one was obtained from 4-butoxyaniline.

(2,2-Diethoxyethyl)-(1,4-dioxaspiro[4.5]dec-8-yl)-amine
1,4-Dioxaspiro[4.5]decan-8-one (1.0 g) was reacted with 2,2-diethoxyethylamine (0.85 g) by method A. The product with the molecular weight of 273.38 (C$_{14}$H$_{27}$NO$_4$) was obtained in this way; MS (ESI): 274 ([M+H]$^+$).

6-Cyclopentyloxypyridin-3-ylamine

A mixture of 5-nitropyridin-2-ol (14.0 g), bromocyclopentane (8.0 g), potassium carbonate (14 g) and DMF (200 mL) was heated at 80° C. for 6 hours. After cooling, the reaction mixture was diluted with water and extracted with ethyl acetate. The organic phase was washed with water, dried over magnesium sulfate and concentrated. The residue was purified by chromatography on silica gel. The resulting product (2-cyclopentyloxy-5-nitropyridine) was hydrogenated in ethanol using palladium(II) hydroxide as catalyst. The product with the molecular weight of 178.24 (C$_{10}$H$_{14}$N$_2$O) was obtained in this way; MS (ESI): 179 (M+H+).

4-Cyclopentyloxyaniline

A mixture of 4-nitrophenol (63.7 g), bromocyclopentane (68.2 g), potassium carbonate (63.3 g) and DMF (300 mL) was heated at 80° C. for 24 hours. After cooling, it was diluted with water and extracted with ethyl acetate. The organic phase was washed with water, dried over magnesium sulfate and concentrated. The residue was hydrogenated in ethanol using palladium(II) hydroxide as catalyst. The product with the molecular weight of 177.25 (C$_{11}$H$_{15}$NO) was obtained in this way; MS (ESI): 178 (M+H+).

Example 2

Trans-1-(4-cyclopentyloxy-phenyl)-3-[4-(2-dimethylaminoethoxy)cyclohexyl]-1,3-dihydroimidazol-2-one

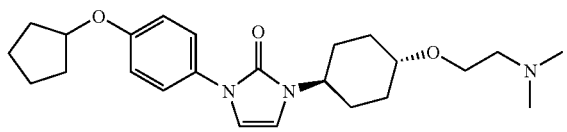

Sodium hydride (42 mg) was added to a mixture of trans-1-(4-cyclopentyloxy-phenyl)-3-(4-hydroxycyclohexyl)-1,3-dihydroimidazol-2-one (0.30 g) and DMF (10 ml) and, after gas evolution ceased, dimethylaminoethyl chloride (94 mg) was added. After eight hours, the reaction solution was diluted with water, and the mixture was extracted with ethyl acetate. The organic phase was dried over magnesium sulfate, filtered and concentrated. The residue was purified by preparative HPLC. The product with the molecular weight of 413.56 ($C_{24}H_{35}N_3O_3$) was obtained in this way; MS (ESI): 414 ([M+H]$^+$).

Trans-1-(4-cyclopentyloxyphenyl)-3-(4-hydroxycyclohexyl)-1,3-dihydroimidazol-2-one Trans-4-aminocyclohexanol was reacted by method B with CDI and (4-cyclopentyloxyphenyl)(2,2-diethoxyethyl)amine. The isolated crude product was mixed with DMF (2 ml) and TFA (2 ml) and left to stand for 12 hours. The reaction solution was diluted with water, and the mixture was extracted with ethyl acetate. The organic phase was dried over magnesium sulfate, filtered and concentrated. The residue was purified by preparative HPLC. The product with the molecular weight of 342.44 ($C_{20}H_{26}N_2O_3$) was obtained in this way; MS (ESI): 343 ([M+H]$^+$).

(4-Cyclopentyloxyphenyl)(2,2-diethoxyethyl)amine

A suspension of 4-cyclopentyloxyaniline (8.86 g), bromoacetaldehyde diethyl acetal (13 g), potassium carbonate (13.8 g) and dimethylformamide (100 ml) was heated at 80° C. for 6 hours. Cooling was followed by filtration and concentration of the filtrate. The residue was purified by chromatography on silica gel (eluent: heptane/ethyl acetate 2:1). The product with the molecular weight of 293.41 ($C_{17}H_{27}NO_3$) was obtained in this way; MS (ESI): 294 ([M+H]$^+$).

The following compounds were prepared by method A using the appropriate ketones and amines:

| Ex. No. | Structure | Molecular formula | Molecular weight | ESI-MS [M + H]$^+$ |
|---|---|---|---|---|
| 3 | 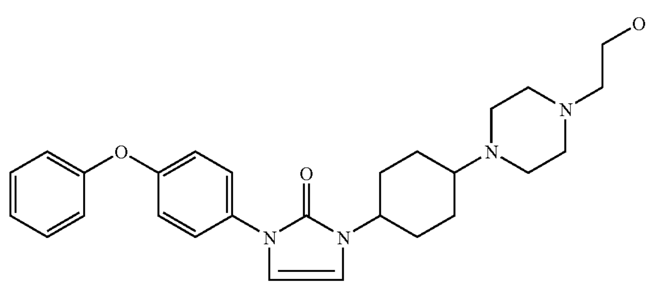 | C27H34N4O3 | 462.60 | 463 |
| 4 | 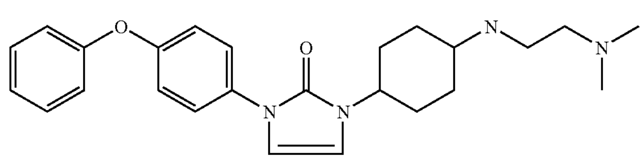 | C25H32N4O2 | 420.56 | 421 |
| 5 | 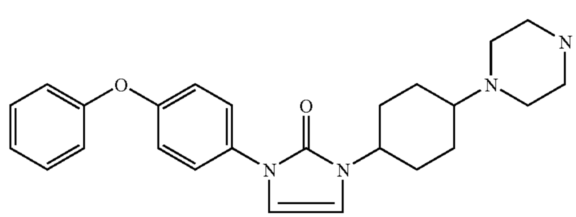 | C25H30N4O2 | 418.54 | 419 |
| 6 | 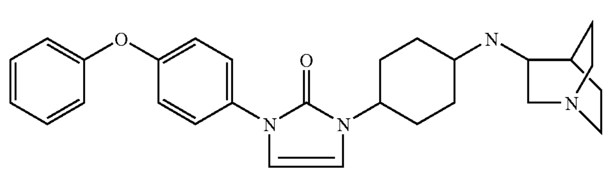 | C28H32N4O2 | 458.61 | 459 |

-continued

| Ex. No. | Structure | Molecular formula | Molecular weight | ESI-MS [M + H]+ |
|---|---|---|---|---|
| 7 | 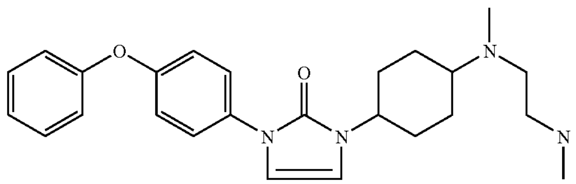 | C25H32N4O2 | 420.56 | 421 |
| 8 | 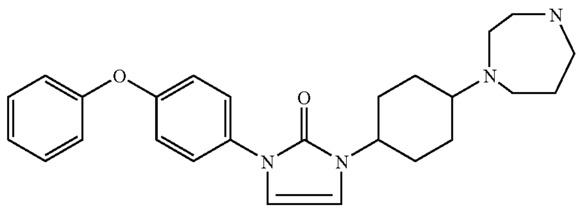 | C26H32N4O2 | 432.57 | 433 |
| 9 | 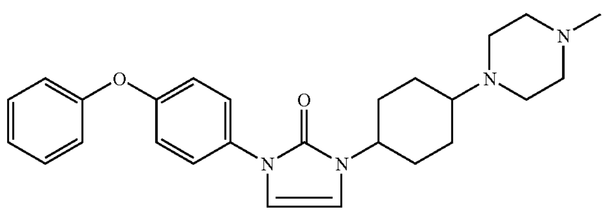 | C26H32N4O2 | 432.57 | 433 |
| 10 | 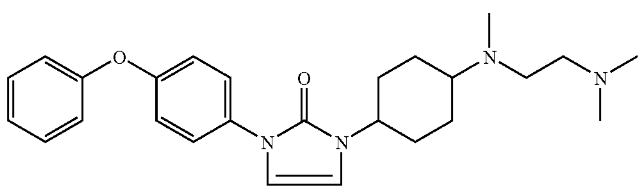 | C26H34N4O2 | 434.59 | 435 |
| 11 | 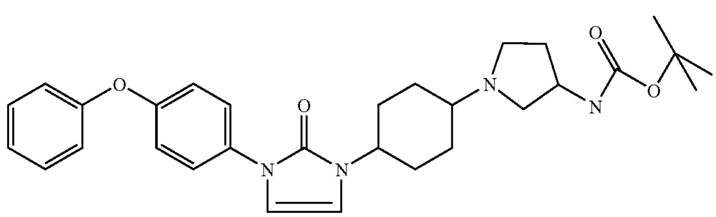 | C30H38N4O4 | 518.66 | 519 |
| 12 | 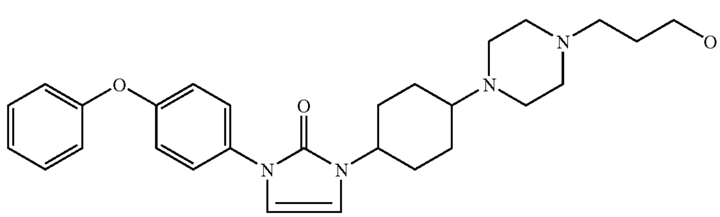 | C28H36N4O3 | 476.62 | 477 |
| 13 | 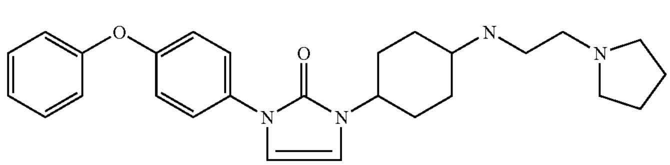 | C27H34N4O2 | 446.60 | 447 |

-continued

| Ex. No. | Structure | Molecular formula | Molecular weight | ESI-MS [M + H]+ |
|---|---|---|---|---|
| 14 | 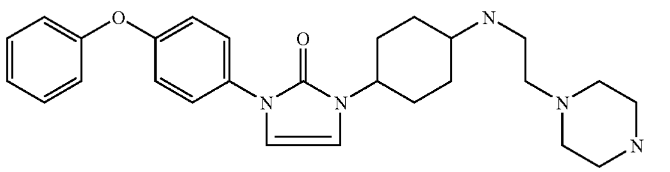 | C27H35N5O2 | 461.61 | 462 |
| 15 | 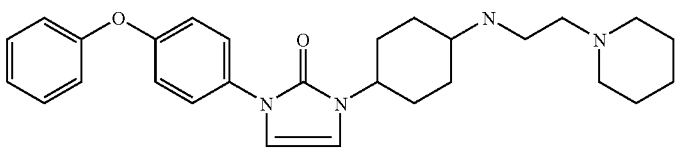 | C28H36N4O2 | 460.62 | 461 |
| 16 | 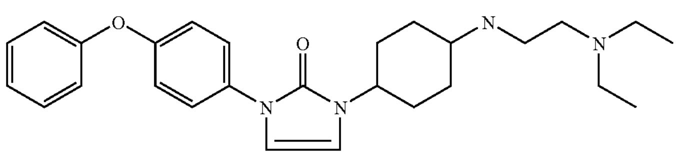 | C27H36N4O2 | 448.61 | 449 |
| 17 | 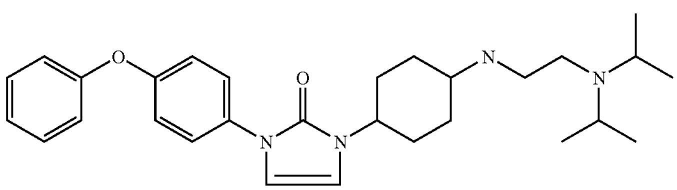 | C29H40N4O2 | 476.67 | 477 |
| 18 | 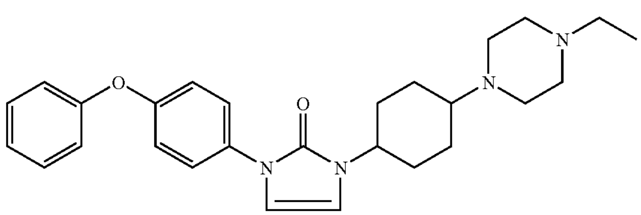 | C27H34N4O2 | 446.60 | 447 |
| 19 | 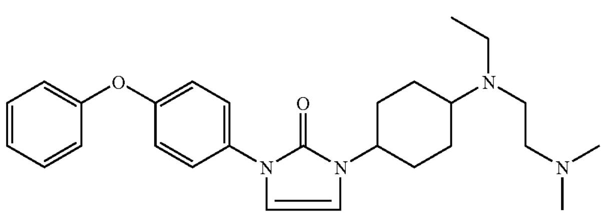 | C27H36N4O2 | 448.61 | 449 |
| 20 | 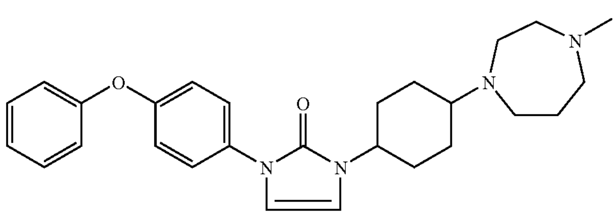 | C27H34N4O2 | 446.60 | 447 |
| 21 | 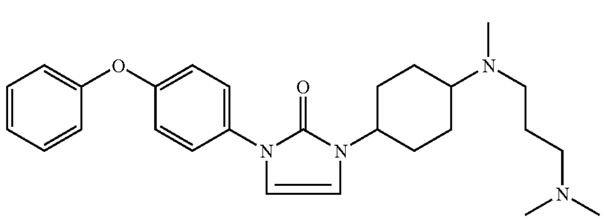 | C27H36N4O2 | 448.61 | 449 |

-continued

| Ex. No. | Structure | Molecular formula | Molecular weight | ESI-MS [M + H]+ |
|---|---|---|---|---|
| 22 | 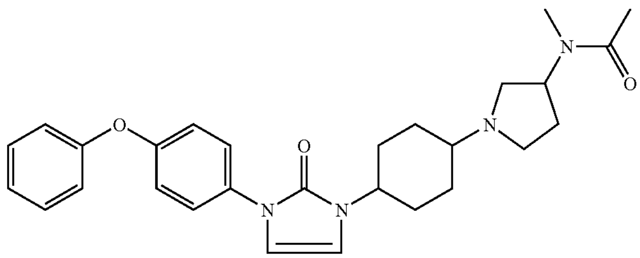 | C28H34N4O3 | 474.61 | 475 |
| 23 | 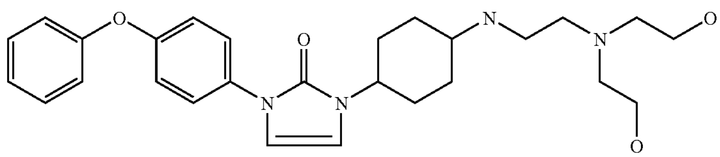 | C27H36N4O4 | 480.61 | 481 |
| 24 | 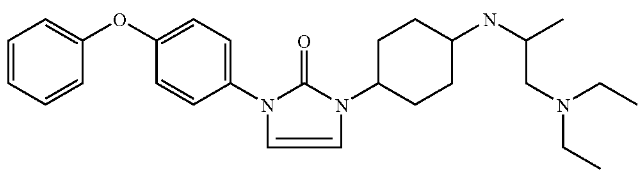 | C28H38N4O2 | 462.64 | 463 |
| 25 | 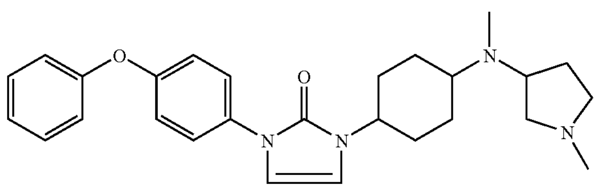 | C27H34N4O2 | 446.60 | 447 |
| 26 | 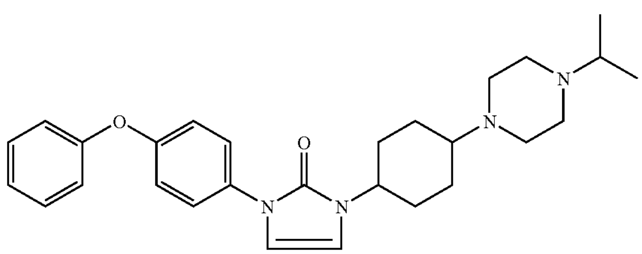 | C28H36N4O2 | 460.62 | 461 |
| 27 | 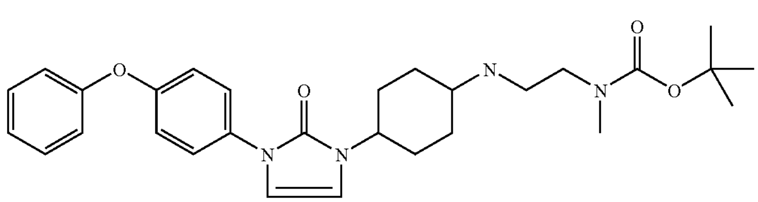 | C29H38N4O4 | 506.65 | 507 |
| 28 | 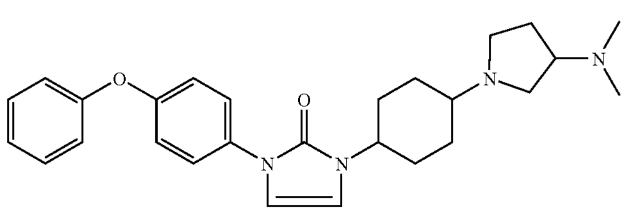 | C27H34N4O2 | 446.60 | 447 |

-continued
| Ex. No. | Structure | Molecular formula | Molecular weight | ESI-MS [M + H]+ |
|---|---|---|---|---|
| 29 | 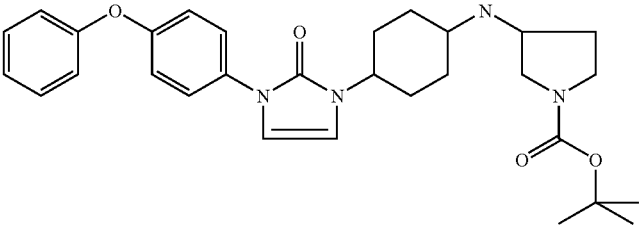 | C20H38N4O4 | 518.66 | 519 |
| 30 | 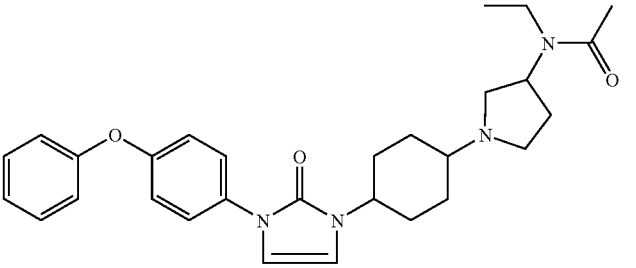 | C29H36N4O3 | 488.64 | 489 |
| 31 | 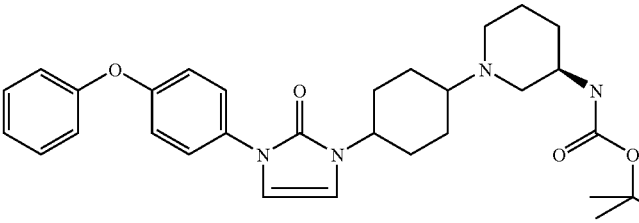 | C31H40N4O4 | 532.69 | 533 |
| 32 | 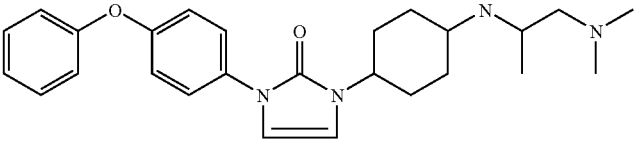 | C26H34N4O2 | 434.59 | 435 |
| 33 | 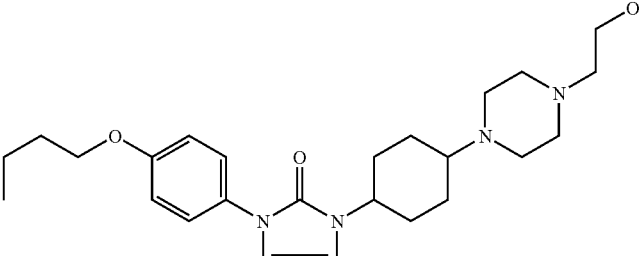 | C25H38N4O3 | 442.61 | 443 |
| 34 | 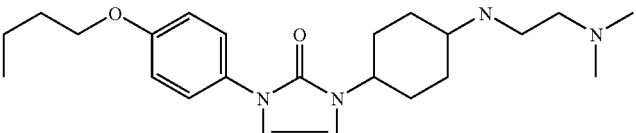 | C23H36N4O2 | 400.57 | 401 |
| 35 | 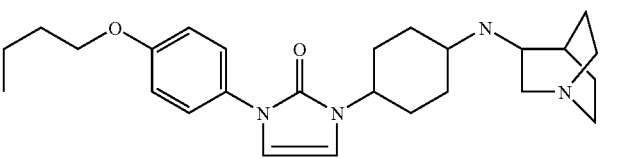 | C26H38N4O2 | 438.62 | 439 |

-continued

| Ex. No. | Structure | Molecular formula | Molecular weight | ESI-MS [M + H]+ |
|---|---|---|---|---|
| 36 | 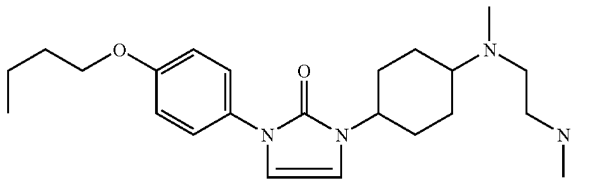 | C23H36N4O2 | 400.57 | 401 |
| 37 | 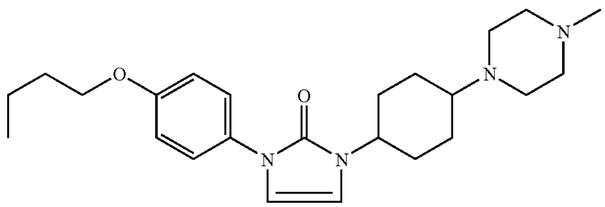 | C24H36N4O2 | 412.58 | 413 |
| 38 | 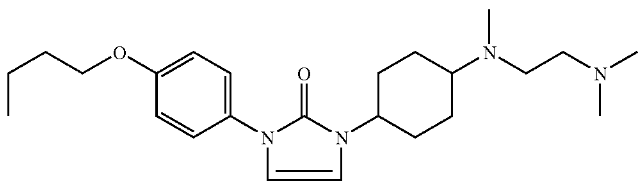 | C24H38N4O2 | 414.60 | 415 |
| 39 | 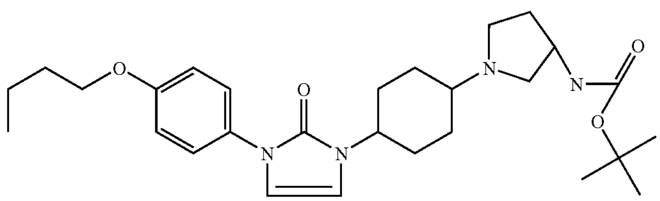 | C28H42N4O4 | 498.67 | 499 |
| 40 | 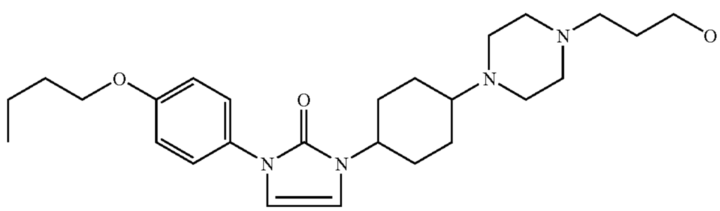 | C26H40N4O3 | 456.63 | 457 |
| 41 | 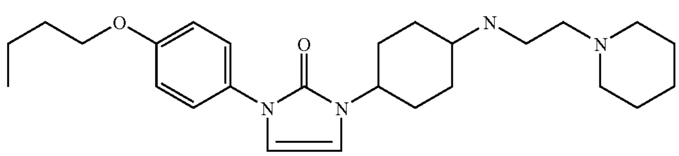 | C26H40N4O2 | 440.63 | 441 |
| 42 | 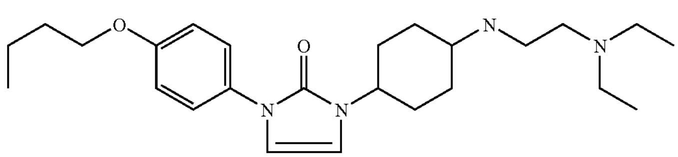 | C25H40N4O2 | 428.62 | 429 |
| 43 | 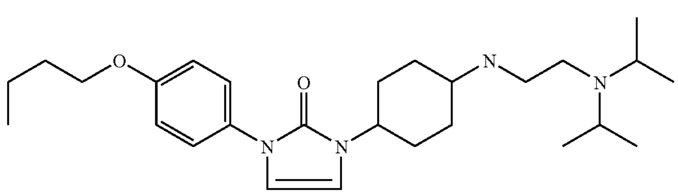 | C27H44N4O2 | 456.68 | 457 |

-continued

| Ex. No. | Structure | Molecular formula | Molecular weight | ESI-MS [M + H]+ |
|---|---|---|---|---|
| 44 | 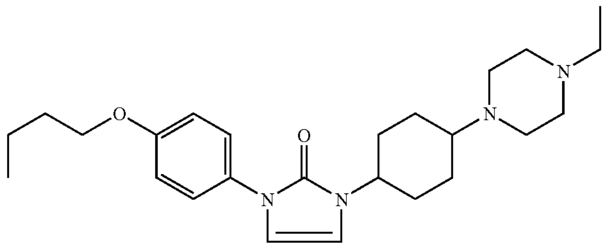 | C25H38N4O2 | 426.61 | 427 |
| 45 | 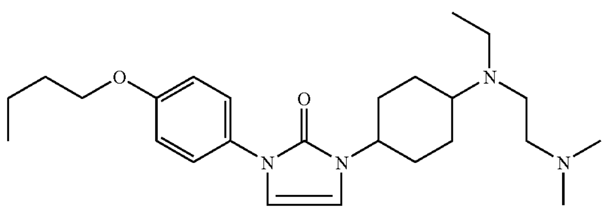 | C25H40N4O2 | 428.62 | 429 |
| 46 | 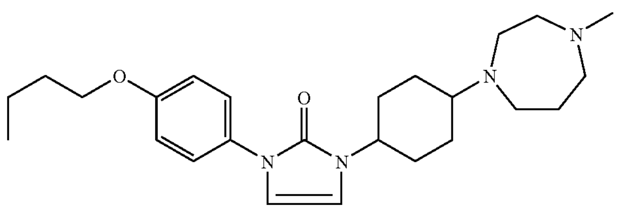 | C25H38N4O2 | 426.61 | 427 |
| 47 | 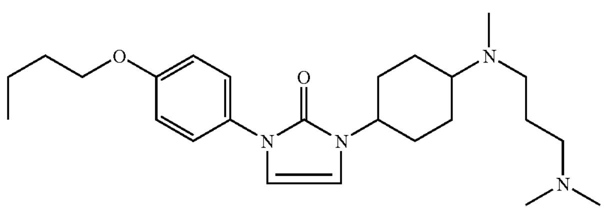 | C25H40N4O2 | 428.62 | 429 |
| 48 | 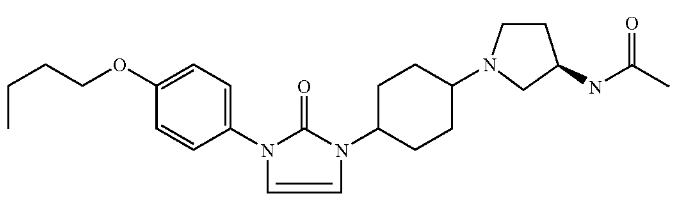 | C25H36N4O3 | 440.59 | 441 |
| 49 | 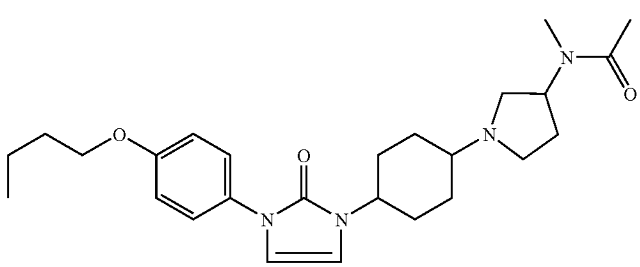 | C26H38N4O3 | 454.62 | 455 |
| 50 | 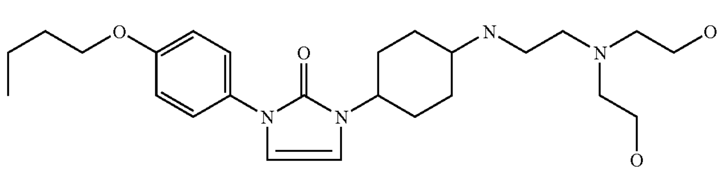 | C25H40N4O4 | 460.62 | 461 |

-continued
| Ex. No. | Structure | Molecular formula | Molecular weight | ESI-MS [M + H]+ |
|---|---|---|---|---|
| 51 | 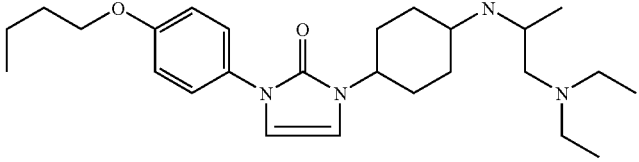 | C26H42N4O2 | 442.65 | 443 |
| 52 | 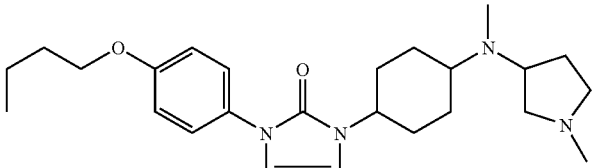 | C25H38N4O2 | 426.61 | 427 |
| 53 | 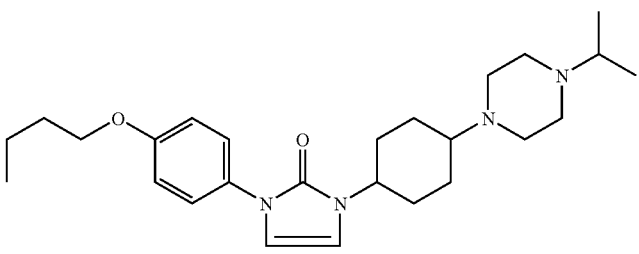 | C26H40N4O2 | 440.63 | 441 |
| 54 | 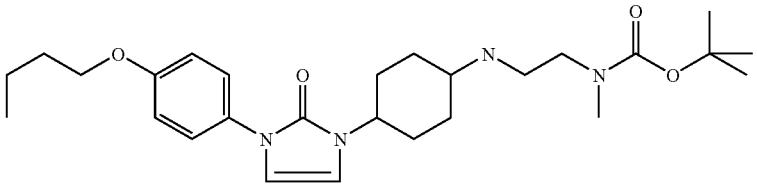 | C27H42N4O4 | 486.66 | 487 |
| 55 | 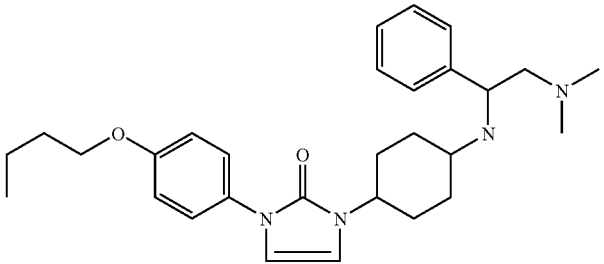 | C29H40N4O2 | 476.67 | 477 |
| 56 | 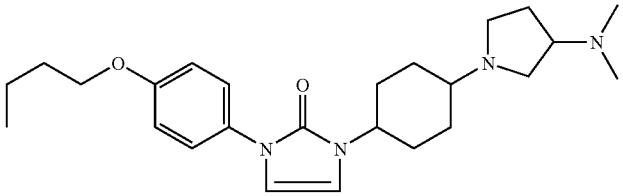 | C25H38N4O2 | 426.61 | 427 |
| 57 | 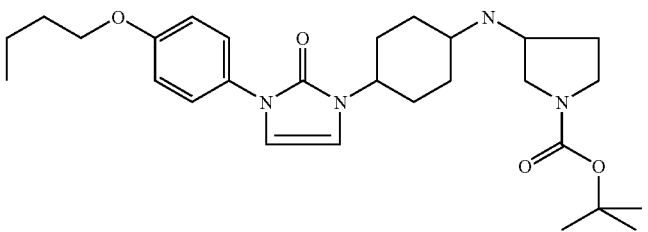 | C28H42N4O4 | 498.67 | 499 |

| Ex. No. | Structure | Molecular formula | Molecular weight | ESI-MS [M + H]+ |
|---|---|---|---|---|
| 58 | 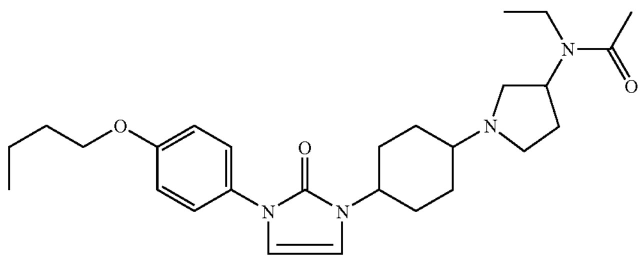 | C27H40N4O3 | 468.64 | 469 |
| 59 | 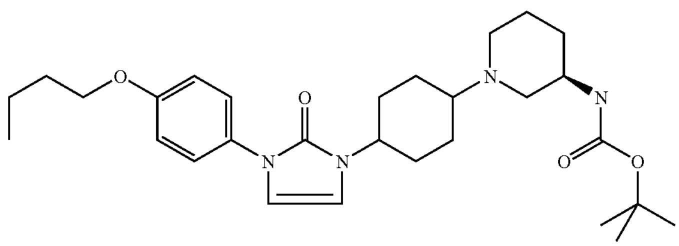 | C29H44N4O4 | 512.70 | 513 |
| 60 | 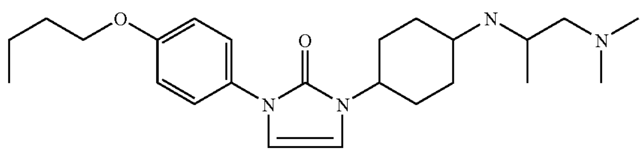 | C24H38N4O2 | 414.60 | 415 |
| 61 | 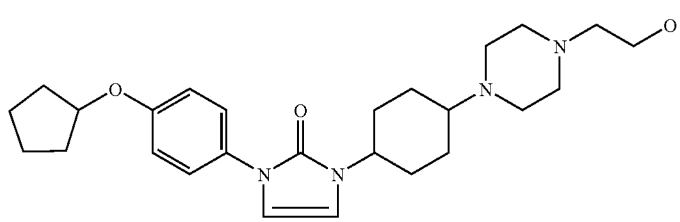 | C26H38N4O3 | 454.62 | 455 |
| 62 | 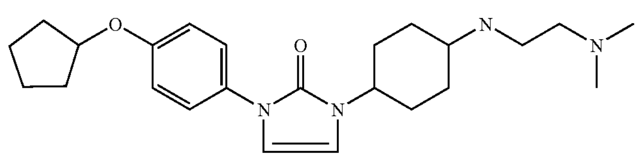 | C24H36N4O2 | 412.58 | 413 |
| 63 | 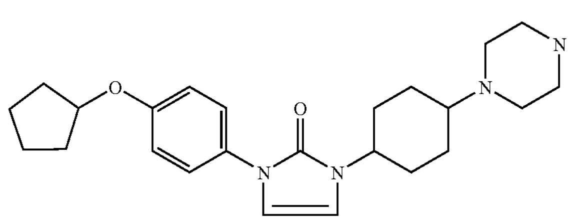 | C24H34N4O2 | 410.56 | 411 |
| 64 | 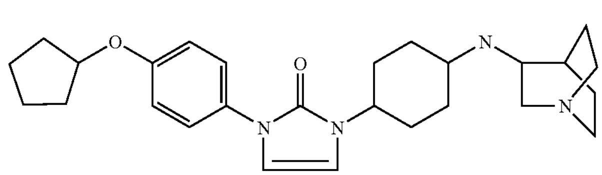 | C27H38N4O2 | 450.63 | 451 |

-continued
| Ex. No. | Structure | Molecular formula | Molecular weight | ESI-MS [M + H]+ |
|---|---|---|---|---|
| 65 | 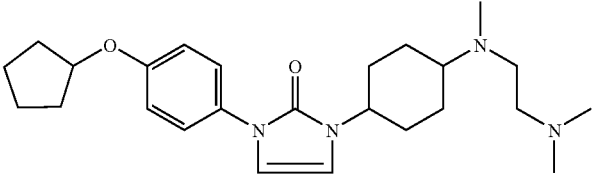 | C24H36N4O2 | 412.58 | 413 |
| 66 | 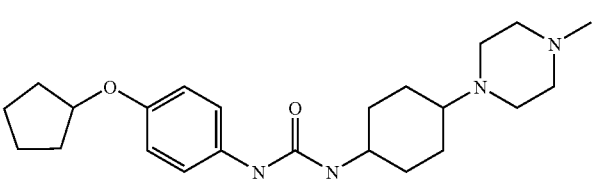 | C25H36N4O2 | 424.59 | 425 |
| 67 | 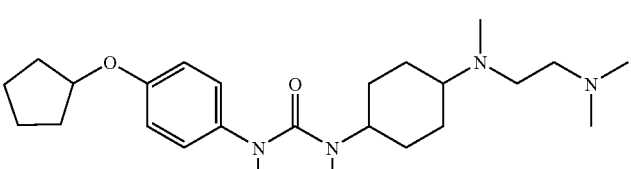 | C25H38N4O2 | 426.61 | 427 |
| 68 | 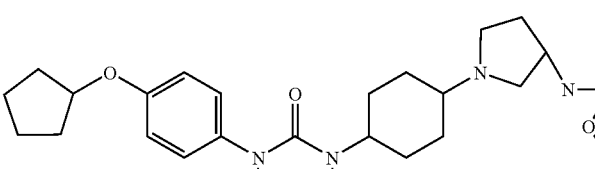 | C29H42N4O4 | 510.68 | 511 |
| 69 | 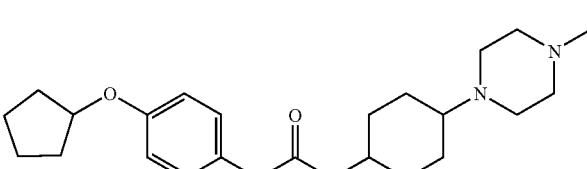 | C27H40N4O3 | 468.64 | 469 |
| 70 | 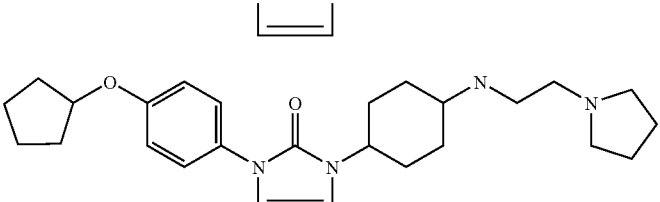 | C26H38N4O2 | 428.62 | 439 |
| 71 | 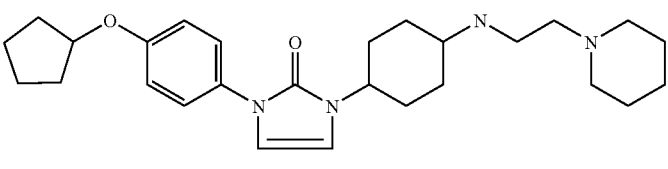 | C27H40N4O2 | 452.65 | 453 |
| 72 | 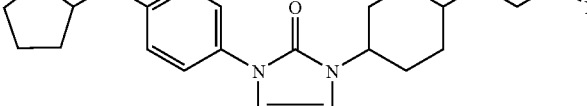 | C26H40N4O2 | 440.63 | 441 |

-continued
| Ex. No. | Structure | Molecular formula | Molecular weight | ESI-MS [M + H]+ |
|---|---|---|---|---|
| 73 | 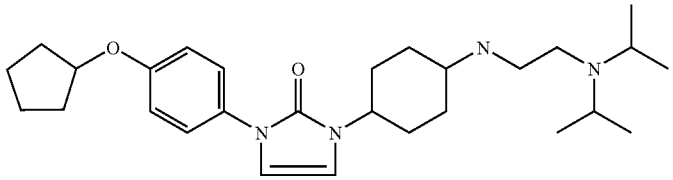 | C28H44N4O2 | 468.69 | 469 |
| 74 | 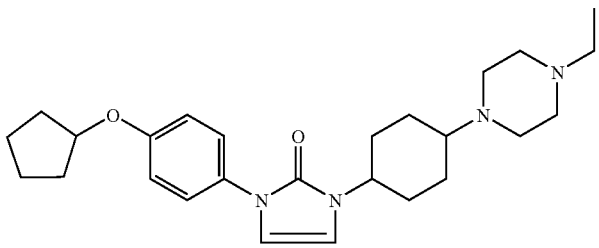 | C26H38N4O2 | 438.62 | 439 |
| 75 | 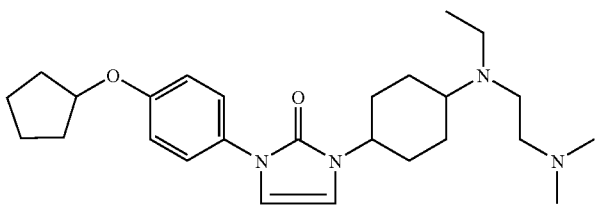 | C26H40N4O2 | 440.63 | 441 |
| 76 | 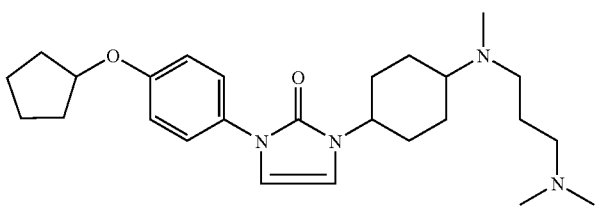 | C26H40N4O2 | 440.63 | 441 |
| 77 | 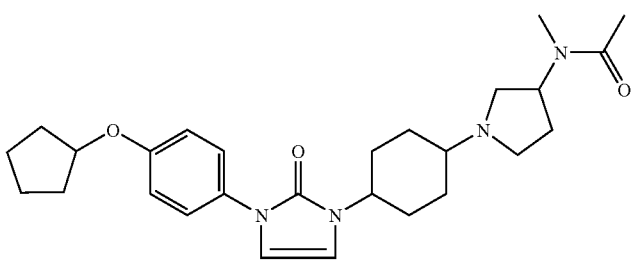 | C27H38N4O3 | 466.63 | 467 |
| 78 | 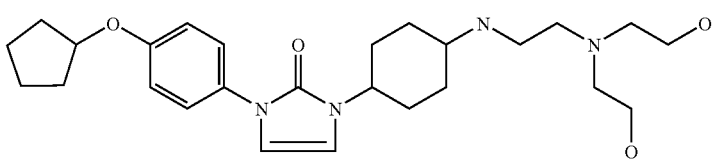 | C26H40N4O4 | 472.63 | 473 |
| 79 | 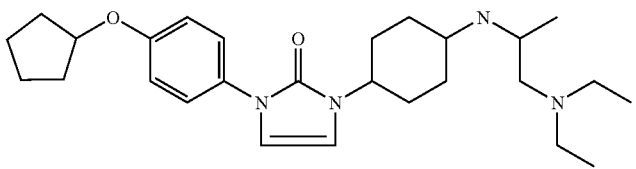 | C27H42N4O2 | 454.66 | 455 |

-continued

| Ex. No. | Structure | Molecular formula | Molecular weight | ESI-MS [M + H]+ |
|---|---|---|---|---|
| 80 | 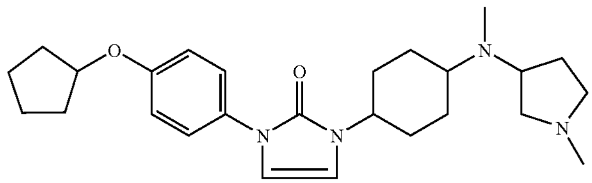 | C26H38N4O2 | 438.62 | 439 |
| 81 | 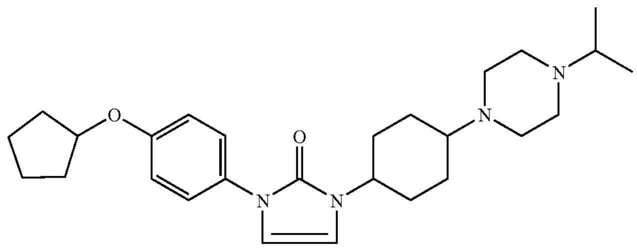 | C27H40N4O2 | 452.65 | 453 |
| 82 | 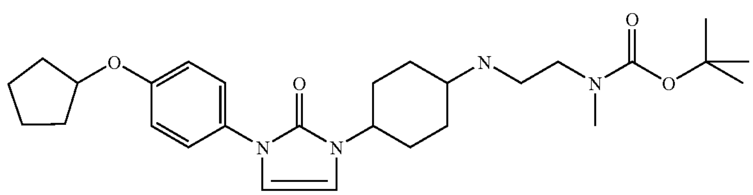 | C28H42N4O4 | 498.67 | 499 |
| 83 | 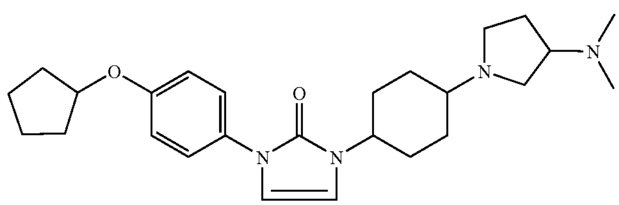 | C26H38N4O2 | 438.62 | 439 |
| 84 | 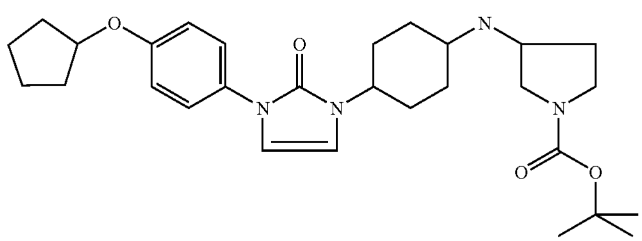 | C29H42N4O4 | 510.68 | 511 |
| 85 | 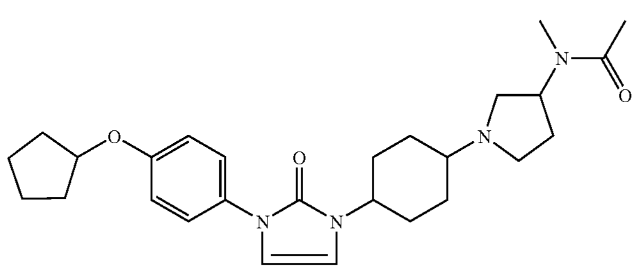 | C28H40N4O3 | 480.66 | 481 |

-continued
| Ex. No. | Structure | Molecular formula | Molecular weight | ESI-MS [M + H]+ |
|---|---|---|---|---|
| 86 | 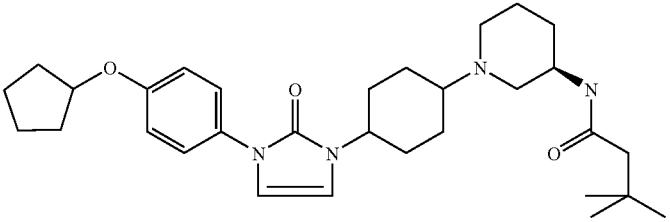 | C30H44N4O4 | 524.71 | 525 |
| 87 | 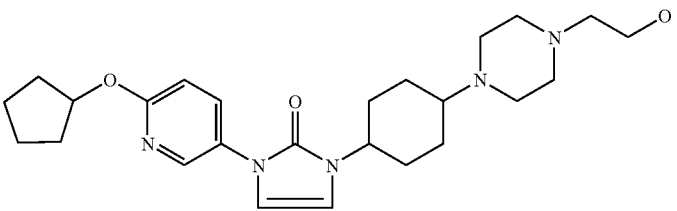 | C25H37N4O3 | 455.61 | 456 |
| 88 | 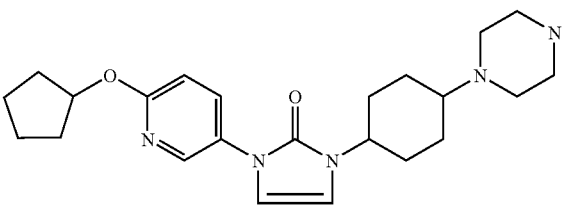 | C23H33N5O2 | 411.55 | 412 |
| 89 | 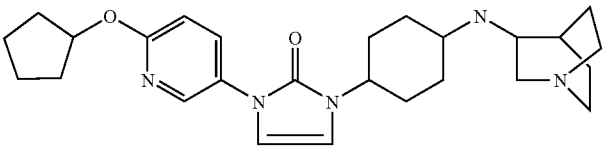 | C26H37N5O2 | 451.62 | 452 |
| 90 | 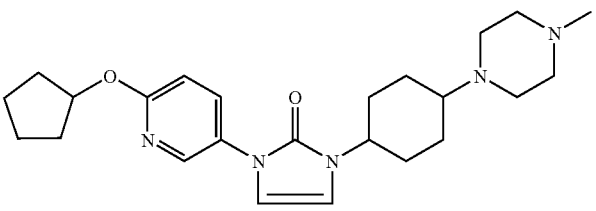 | C24H35N5O2 | 425.58 | 426 |
| 91 | 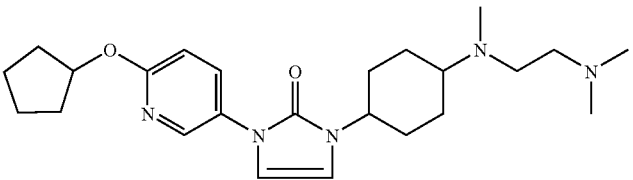 | C24H37N5O2 | 427.59 | 428 |
| 92 | 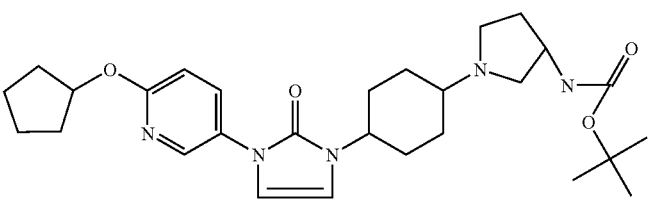 | C28H41N5O4 | 511.67 | 512 |

-continued

| Ex. No. | Structure | Molecular formula | Molecular weight | ESI-MS [M + H]+ |
|---|---|---|---|---|
| 93 | 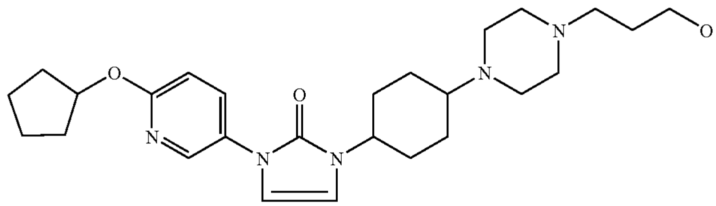 | C26H39N5O3 | 469.63 | 470 |
| 94 | 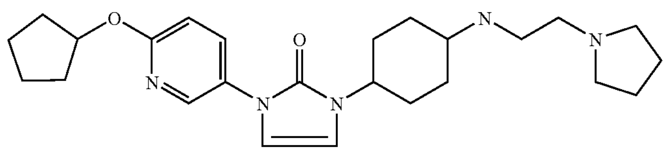 | C25H37N5O2 | 439.61 | 440 |
| 95 | 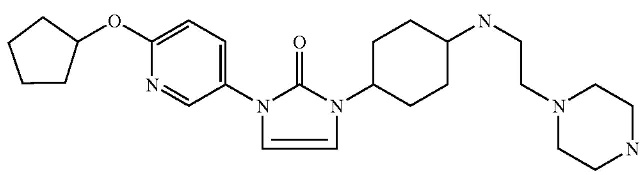 | C25H38N6O2 | 454.62 | 455 |
| 96 | 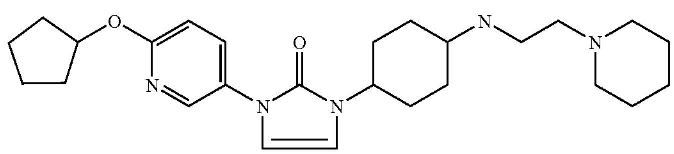 | C26H39N5O2 | 453.63 | 454 |
| 97 | 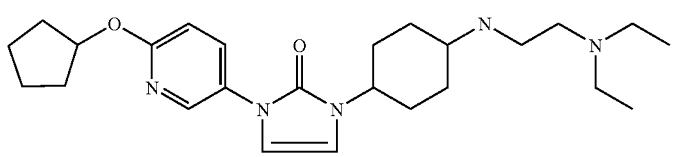 | C25H39N5O2 | 441.62 | 442 |
| 98 | 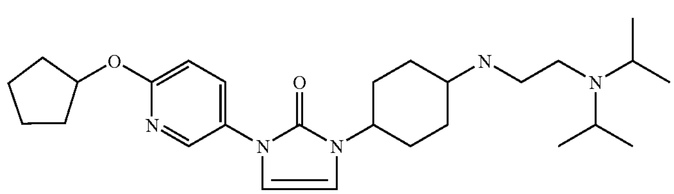 | C27H43N5O2 | 469.68 | 470 |
| 99 | 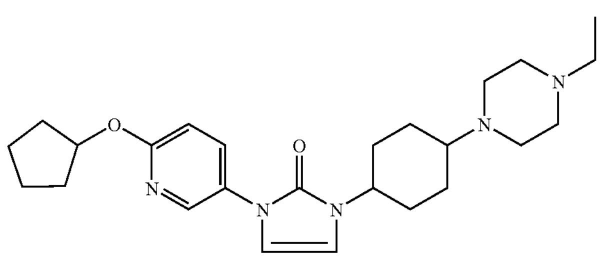 | C25H37N5O2 | 439.61 | 440 |
| 100 | 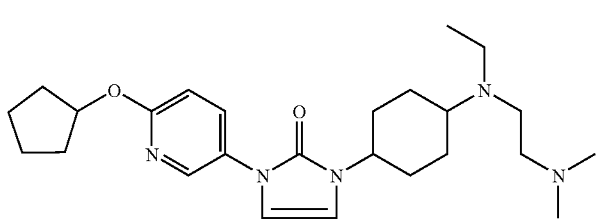 | C25H39N5O2 | 441.62 | 442 |

-continued

| Ex. No. | Structure | Molecular formula | Molecular weight | ESI-MS [M + H]+ |
|---|---|---|---|---|
| 101 | 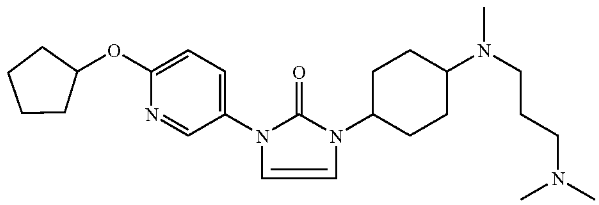 | C25H39N5O2 | 441.62 | 442 |
| 102 | 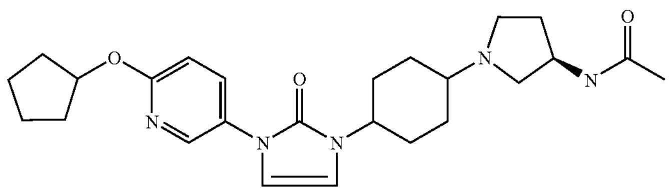 | C25H35N5O3 | 453.59 | 454 |
| 103 | 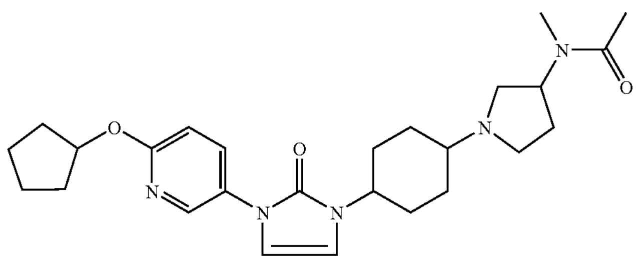 | C26H37N5O3 | 467.62 | 468 |
| 104 | 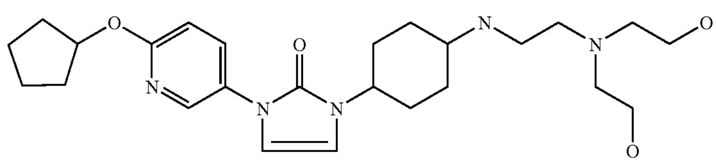 | C25H39N5O2 | 473.62 | 474 |
| 105 | 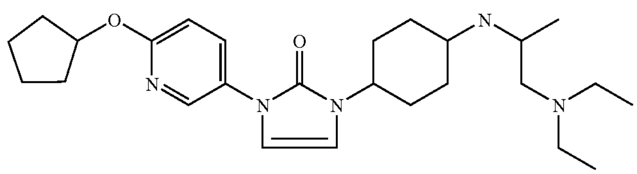 | C26H41N5O2 | 455.65 | 456 |
| 106 | 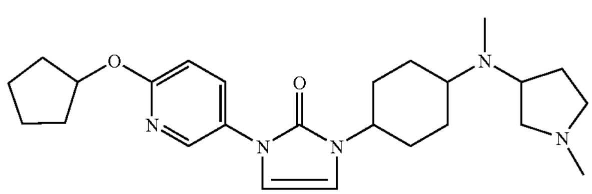 | C25H37N5O2 | 439.61 | 440 |
| 107 | 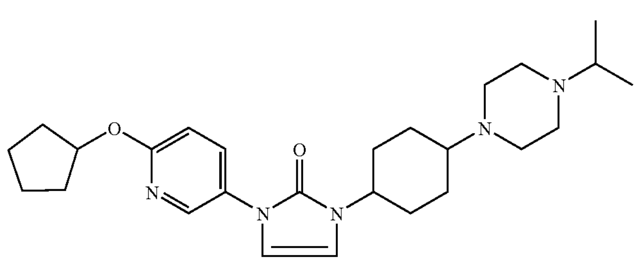 | C26H39N5O2 | 453.63 | 454 |

-continued

| Ex. No. | Structure | Molecular formula | Molecular weight | ESI-MS [M + H]+ |
|---|---|---|---|---|
| 108 | 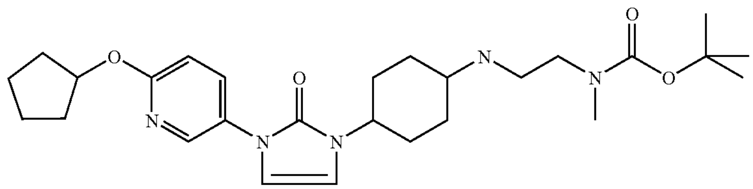 | C27H41N5O4 | 499.66 | 500 |
| 109 | 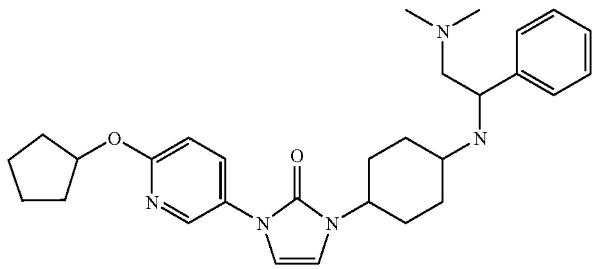 | C29H39N5O2 | 489.67 | 490 |
| 110 | 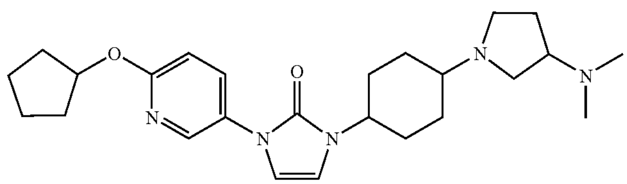 | C25H37N5O2 | 439.61 | 440 |
| 111 | 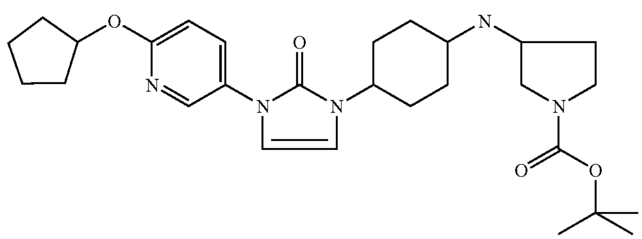 | C28H41N5O4 | 511.67 | 512 |
| 112 | 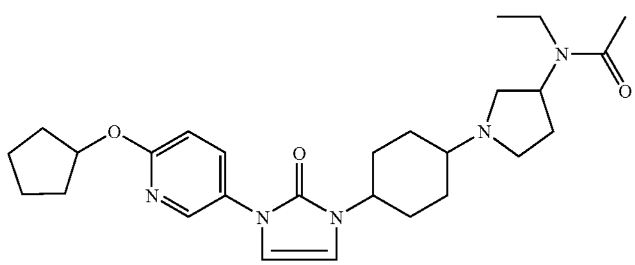 | C27H39N5O3 | 481.64 | 482 |
| 113 | 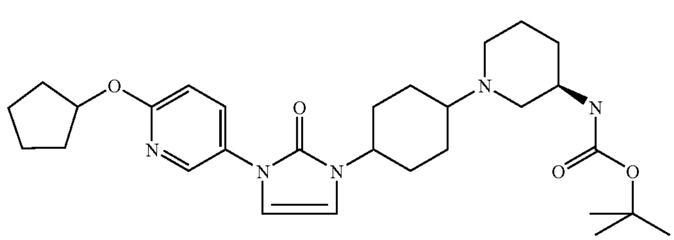 | C29H43N5O4 | 525.70 | 526 |
| 114 | 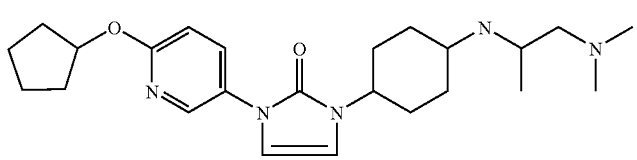 | C24H37N5O2 | 427.59 | 428 |

-continued

| Ex. No. | Structure | Molecular formula | Molecular weight | ESI-MS [M + H]+ |
|---|---|---|---|---|
| 115 | 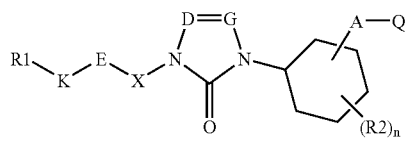 | C26H38N4O2 | 438.62 | 439 |
| 116 | 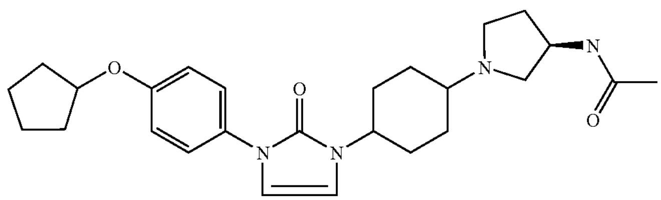 | C26H36N4O3 | 452.60 | 453 |
| 117 | 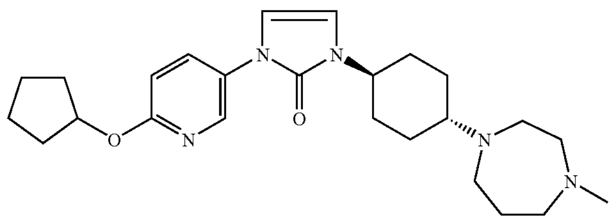 | C25H37N5O2 | 439.61 | 440 |
| 118 | 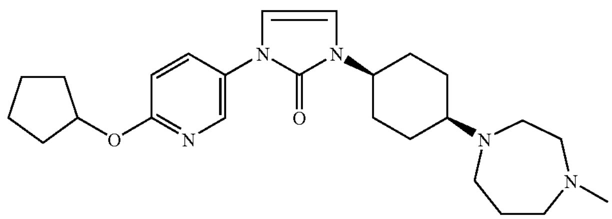 | C25H37N5O2 | 439.61 | 440 |

What is claimed is:

1. A compound of the formula I, in which the meanings are

R1 H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, a 3 to 10-membered mono-, bi- or spirocyclic ring which may include 0 to 4 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, S—$(C_1-C_8)$-alkyl, $(C_1-C_4)$-alkoxy-$(C_1-C_4)$-alkyl, $(C_0-C_8)$-alkylene-aryl, oxo, CO(R3), CON(R4)(R5), hydroxy, hydroxy-$(C_1-C_4)$-alkyl, COO(R6), N(R7)CO$(C_1-C_6)$-alkyl, N(R8)(R9) or $SO_2CH_3$;

R3, R4, R5, R6, R7, R8, R9, independently of one another H, $(C_1-C_6)$-alkyl;

K a group of the formula —$(CR10R11)_z$—, in which one or more —(CR10R11)— groups may be replaced by Z, a bond, C≡C, C=C;

Z O, CO, N(R59), S, SO, $SO_2$;

R10, R11 independently of one another H, $(C_1-C_8)$-alkyl, hydroxy-$(C_1-C_4)$-alkyl, hydroxy, $(C_1-C_4)$-alkoxy-$(C_1-C_4)$-alkyl, where R10 and R11 in the z groups may in each case have the same or different meanings;

z 1, 2, 3, 4, 5, 6;

R59 H, $(C_1-C_8)$-alkyl;

E 3–14 membered bivalent carbo- or heterocyclic ring structure having 0–4 heteroatoms from the group of N, O and S, which may optionally have substituents from the group of H, F, Cl, Br, I, OH, $CF_3$, $NO_2$, CN, $OCF_3$, oxo, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R12)(R13), $SO_2$—$CH_3$, COOH, COO—$(C_1-C_6)$-alkyl, CON(R14)(R15), N(R16)CO(R17), N(R18)$SO_2$(R19), CO(R20) and be mono- or bicyclic;

R12, R13, R14, R15, R16, R18 independently of one another H, $(C_1-C_8)$-alkyl;

or

R12 and R13, R14 and R15 independently of one another, optionally together with the nitrogen atom to which they are bonded, a 5–6 membered ring which, apart from the nitrogen atom, may also include 0–1 further heteroatoms from the group of N-$(C_1-C_6)$-alkyl, oxygen and sulfur;

R17, R19, R20 independently of one another H, $(C_1-C_8)$-alkyl, aryl;

X a bond, a group of the formula —$(CR21R22)_y$—, in which one or more —(CR21R22)— groups may be replaced by Y;

Y O, CO, N(R23), S, SO, $SO_2$;

R21, R22 independently of one another H, $(C_1-C_4)$-alkyl, where R21 and R22 in the y groups may in each case have the same or different meanings;

y 1, 2, 3, 4, 5, 6;

R23 H, $(C_1-C_8)$-alkyl;

D, G CH or N;

R2 OH, O—$(C_1-C_6)$-alkyl, O—$(C_1-C_4)$-alkoxy-$(C_1-C_4)$-alkyl, $(C_1-C_6)$-alkyl;

n 0, 1, 2, 3, 4;

Q N(R24)(R25), or a 3 to 8-membered ring which may include 0 to 3 heteroatoms selected from the group of oxygen, nitrogen and sulfur, where the ring system may additionally be substituted by $(C_0-C_4)$-alkylene-N(R24)(R25), F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, $(C_0-C_8)$-alkylene-aryl, oxo, CO(R26), CON(R27)(R28), hydroxy, hydroxy-$(C_1-C_4)$-alkyl, COO(R29), N(R30)CO$(C_1-C_6)$-alkyl or $SO_2CH_3$;

R26, R27, R28, R29, R30 independently of one another H, $(C_1-C_6)$-alkyl;

A a group of the formula —$(C(R31)(R32))_m$—, in which 0–2 members may be replaced by an element from the group of O, S, N(R33), CO, $SO_2$;

m 0, 1, 2, 3, 4, 5;

R31, R32, R33 independently of one another H, $(C_1-C_6)$-alkyl, aryl;

R24, R25 independently of one another H, $(C_1-C_8)$-alkyl, —$(CR34R35)_o$—R36, $(C_1-C_4)$-alkoxy-$(C_1-C_4)$-alkyl, $(C_3-C_8)$-alkenyl, $(C_3-C_8)$-alkynyl, CO—$(C_1-C_8)$-alkyl, —CO—$(CH_2)_n$—R36, CO(C(R37)(R38))$_q$N(R39)(R40), CO(C(R41)(R42))$_s$O(R43); or R24 and R25 form together with the nitrogen atom to which they are bonded a 4 to 10-membered mono-, bi- or spirocyclic ring which, apart from the nitrogen atom, may include 0 to 4 additional heteroatoms selected from the group of oxygen, nitrogen and sulfur, where the heterocyclic ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, $(C_0-C_8)$-alkylene-aryl, oxo, CO(R44), CON(R45)(R46), hydroxy, COO(R47), N(R48)CO$(C_1-C_6)$-alkyl, N(R49)(R50) or $SO_2CH_3$;

o, 1, 2, 3, 4, 5, 6;

q, s independently of one another 0, 1, 2, 3, 4;

R34, R35 independently of one another H, $(C_1-C_8)$-alkyl, hydroxy-$(C_1-C_4)$-alkyl, OH, $(C_1-C_4)$-alkoxy-$(C_1-C_4)$-alkyl;

R37, R38, R39, R40, R41, R42, R43, R44, R45, R46, R47, R48, R49, R50 independently of one another H, $(C_1-C_6)$-alkyl;

R39 and R40, R45 and R46, R49 and R50 independently of one another, optionally together with the nitrogen atom to which they are bonded a 5–6 membered ring which, apart from the nitrogen atom, may also include 0–1 further heteroatoms from the group of N-$(C_1-C_6)$-alkyl, oxygen and sulfur;

R36 OH, O—$(C_1-C_6)$-alkyl, O—$(C_0-C_8)$-alkylene-aryl, CON(R51)(R52), N(R53)(R54), 3–12 membered mono-, bi- or spirocyclic ring which may comprise one or more heteroatoms from the group of N, O and S, and the 3–12 membered ring may comprise further substituents such as F, Cl, Br, I, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, O—$(C_0-C_8)$-alkylene-aryl, $(C_0-C_8)$-alkylene-aryl, N(R55)(R56), CO$(C_1-C_6)$-alkyl, COO(R57) and $S(O)_u$(R58);

u 0, 1, 2;

R51, 52 independently of one another H, $(C_1-C_8)$-alkyl, $(C_2-C_6)$-alkenyl, $(C_0-C_8)$-alkylene-aryl;

R53, R54 independently of one another H, $(C_1-C_6)$-alkyl;

R55, R56 independently of one another H, $(C_1-C_8)$-alkyl;

R57 H, $(C_1-C_8)$-alkyl, $(C_2-C_6)$-alkenyl, $(C_0-C_8)$-alkylene-aryl;

R58 $(C_1-C_6)$-alkyl, 5–10 membered aromatic ring system which may comprise 0–2 further heteroatoms from the group of nitrogen, oxygen and sulfur and be substituted by F, Cl, Br, $CF_3$, $NO_2$, CN, $(C_1-C_8)$-alkyl, O—$(C_1-C_8)$-alkyl;

and the physiologically tolerated salts thereof.

2. A compound of the formula I as claimed in claim 1, in which the meanings are

R1 $(C_1-C_8)$-alkyl, $(C_1-C_4)$-alkoxy-$(C_1-C_4)$-alkyl, a 3 to 10-membered mono-, bi- or spirocyclic ring which may include 0 to 3 heteroatoms selected from the group of oxygen, nitrogen and sulfur, where the ring system may additionally be substituted by F, Cl, Br, $CF_3$, CN, $(C_1-C_6)$-alkyl, O—$(C_1-C_8)$-alkyl, $(C_0-C_2)$-alkylene-aryl, oxo, CO(R3), CON(R4)(R5), hydroxy, N(R7)CO$(C_1-C_6)$-alkyl, N(R8)(R9) or $SO_2CH_3$;

R3, R4, R5, R7, R8, R9 independently of one another H, $(C_1-C_8)$-alkyl;

K a bond, $OCH_2$, $CH_2O$, $(C(R10)(R11))_z$, C≡C;

z 1, 2, 3, 4;

R10, R11 independently of one another H, $(C_1-C_8)$-alkyl;

E 3–8 membered bivalent carbo- or heterocyclic ring structure having 0–4 heteroatoms from the group of N, O and S, which may optionally have substituents from the group of H, F, Cl, Br, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, O—$(C_3-C_8)$-cycloalkyl, $(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R12)(R13), $SO_2$—$CH_3$, N(R16)CO(R17), N(R18)$SO_2$(R19), CO(R20) and be mono- or bicyclic;

R12, R13, R16, R18 independently of one another H, $(C_1-C_8)$-alkyl;

R17, R19, R20 independently of one another H, $(C_1-C_8)$-alkyl, aryl;

X a bond, —$CH_2$—$CH_2$—;

D, G either D is N and G is CH or D is CH and G is N or D and G are both CH;

R2 OH, O—$(C_1-C_6)$-alkyl, O—$(C_1-C_4)$-alkoxy-$(C_1-C_4)$-alkyl, $(C_1-C_6)$-alkyl;

n 0, 1, 2;

Q N(R24)(R25), or a 3 to 8-membered monocyclic ring which may include 0 to 3 heteroatoms selected from the group of oxygen, nitrogen and sulfur, where the ring system may be additionally substituted by N(R24)(R25), F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, $(C_0-C_8)$-alkylene-aryl, oxo, CO(R26), CON(R27)(R28), hydroxy, hydroxy-$(C_1-C_4)$-alkyl, COO(R29), N(R30)CO$(C_1-C_6)$-alkyl or $SO_2CH_3$;

R26, R27, R28, R29, R30 independently of one another H, $(C_1-C_6)$-alkyl;

A a group of the formula —$(C(R31)(R32))_m$— in which 0–2 members may be replaced by an element from the group of O, N(R33), CO;

m 0, 1, 2, 3, 4;

R31, R32, R33 independently of one another H, $(C_1-C_6)$-alkyl, aryl;

R24, R25 independently of one another H, $(C_1-C_8)$-alkyl, —$(CH_2)_o$—R36, CO—$(C_1-C_8)$-alkyl, or R24 and R25 form together with the nitrogen atom to which they are bonded a 4 to 10-membered, mono-, bi- or spirocyclic ring which, apart from the nitrogen atom, may include 0 to 2 additional heteroatoms selected from the group of oxygen, nitrogen and sulfur, where the heterocyclic ring system may additionally be substituted by F, Cl, $(C_1-C_6)$-alkyl, O—$(C_1-C_8)$-alkyl, oxo, CO(R44), CON(R45)(R46), hydroxy, N(R48)CO$(C_1-C_6)$-alkyl or N(R49)(R50);

o 0, 1, 2, 3, 4;

R36 OH, 5–10 membered mono- or bicyclic ring which may comprise one or more heteroatoms from the group of N, O and S, and the 5–10 membered ring may comprise further substituents such as F, Cl, Br, OH, $CF_3$, oxo, O—$(C_1-C_6)$-alkyl, $(C_1-C_6)$-alkyl, O—$(C_0-C_2)$-alkylene-aryl, $(C_0-C_2)$-alkylene-aryl and N(R55)(R56);

R44, R45, R46, R48, R49, R50 independently of one another H, $(C_1-C_6)$-alkyl;

R55, R56 independently of one another H, $(C_1-C_8)$-alkyl, and the physiologically tolerated salts thereof.

3. A compound of the formula I as claimed in claim 2, in which the meanings are:

R1 $(C_1-C_8)$-alkyl, $(C_1-C_4)$-alkoxy-$(C_1-C_4)$-alkyl, a 3 to 10-membered mono- or bicyclic ring which may include 0 to 2 heteroatoms selected from the group of oxygen, nitrogen and sulfur, where the ring system may additionally be substituted by F, Cl, Br, $CF_3$, CN, $(C_1-C_6)$-alkyl, O—$(C_1-C_8)$-alkyl, oxo, CO(R3), CON(R4)(R5), N(R7)CO$(C_1-C_6)$-alkyl, or $SO_2CH_3$;

R3, R4, R5, R7, R8, R9 independently of one another H, $(C_1-C_8)$-alkyl;

K a bond, $OCH_2$, $CH_2O$, $(C(R10)(R11))_z$, C≡C;

z 1, 2;

R10, R11 independently of one another H, $(C_1-C_8)$-alkyl;

E particularly preferably 5–7 membered bivalent carbo- or heterocyclic ring structure having 0–2 heteroatoms from the group of N, O and S, which may optionally have substituents from the group of H, F, Cl, Br, OH, $CF_3$, $NO_2$, $OCF_3$, O—$(C_1-C_6)$-alkyl, $(C_1-C_6)$-alkyl, $(C_2-C_6)$-alkenyl, N(R12)(R13), $SO_2$—$CH_3$, CO(R20);

R12, R13 independently of one another H, $(C_1-C_8)$-alkyl;

R20 independently of one another H, $(C_1-C_8)$-alkyl;

X a bond;

D, G both CH;

R2 OH, O—$(C_1-C_6)$-alkyl, O—$(C_1-C_4)$-alkoxy-$(C_1-C_4)$-alkyl, $(C_1-C_6)$-alkyl, preferably O—$(C_1-C_6)$-alkyl, $(C_1-C_6)$-alkyl;

n 0 or 1;

Q N(R24)(R25), or a 3 to 8-membered monocyclic ring which may include 0 to 3 heteroatoms selected from the group of oxygen, nitrogen and sulfur, where the ring system may additionally be substituted by N(R24)(R25), F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, $(C_0-C_8)$-alkylene-aryl, oxo, CO(R26), CON(R27)(R28), hydroxy, hydroxy-$(C_1-C_4)$-alkyl, COO(R29), N(R30)CO$(C_1-C_6)$-alkyl or $SO_2CH_3$; preferably N(R24)(R25), F, Cl, $(C_1-C_6)$-alkyl, O—$(C_1-C_8)$-alkyl, $(C_1-C_4)$-alkoxy-$(C_1-C_4)$-alkyl, $(C_0-C_8)$-alkylene-aryl, oxo, CO(R26), N(R30)CO$(C_1-C_6)$-alkyl or $SO_2CH_3$;

R26, R27, R28, R29, R30 $(C_1-C_6)$-alkyl;

A a group of the formula —$(C(R31)(R32))_m$— in which 1 member may be replaced by an element from the group of O, N(R33);

m 0, 1, 3 or 4;

R31, R32, R33 H;

R24, R25 independently of one another H, $(C_1-C_8)$-alkyl, —$(CH_2)_o$—R36, CO$(C_1-C_8)$-alkyl, or R24 and R25 form together with the nitrogen atom to which they are bonded a 4 to 10-membered mono-, bi- or spirocyclic ring which, apart from the nitrogen atom, may include 0 to 2 additional heteroatoms selected from the group of oxygen, nitrogen and sulfur, where the heterocyclic ring system may additionally be substituted by F, Cl, $(C_1-C_6)$-alkyl, O—$(C_1-C_8)$-alkyl, oxo, CO(R44), CON(R45)(R46), hydroxy, N(R48)CO$(C_1-C_6)$-alkyl or N(R49)(R50); preferably F, $(C_1-C_6)$-alkyl, O—$(C_1-C_8)$-alkyl, oxo, CO(R44), N(R48)CO$(C_1-C_6)$-alkyl or N(R49)(R50);

o 0, 1, 2, 3, 4;

R36 OH, 5–10 membered mono- or bicyclic ring which may comprise one or more heteroatoms from the group of N, O and S, and the 5–10 membered ring may comprise further substituents such as F, Cl, Br, OH, $CF_3$, oxo, O—$(C_1-C_6)$-alkyl, $(C_1-C_6)$-alkyl, O—$(C_0-C_2)$-alkylene-aryl, $(C_0-C_2)$-alkylene-aryl and N(R55)(R56); preferably a 5–8 membered monocyclic ring which may comprise 0–2 heteroatoms from the group of N, O and S, and the 5–8 membered ring may comprise further substituents such as F, oxo, O—$(C_1-C_6)$-alkyl, $(C_1-C_6)$-alkyl, $(C_0-C_2)$-alkylene-aryl and N(R55)(R56);

R44, R45, R46, R48, R49, R50 independently of one another H, $(C_1-C_6)$-alkyl;

R55, R56 independently of one another H, $(C_1-C_8)$-alkyl; and the physiologically tolerated salts thereof.

4. A compound of the formula I as claimed in claim 1, in which the radicals R1 and R2, the index n and the groups K, E, X, D=G, Q and A have the following meanings R1 H, $(C_1-C_8)$-alkyl, $(C_1-C_4)$-alkoxy-$(C_1-C_4)$-alkyl, a 3–8 membered monocyclic ring which may include 0 to 3 heteroatoms selected from the group of oxygen, nitrogen and sulfur, where the ring system may additionally be substituted by F, Cl, Br, $(C_1-C_6)$-alkyl, O—$(C_1-C_8)$-alkyl; $(C_1-C_4)$-alkoxy-$(C_1-C_4)$-alkyl;

K O, a bond, C≡C, CO, $OCH_2$, $OCH_2CH_2$;

E a 5–6 membered monocyclic bivalent carbo- or heterocyclic ring structure having 0–2 heteroatoms from the group of N, O and S, which may optionally have substituents from the group of H, F, Cl, Br, oxo, O—$(C_1-C_8)$-alkyl, O—$(C_1-C_4)$-alkoxy-$(C_1-C_4)$-alkyl, $(C_1-C_6)$-alkyl;

X a bond, $CH_2CH_2$, $CH_2CH_2CH_2$, $OCH_2CH_2$;

D=G CH=CH, CH=N, N=CH;

R2 OH, O—($C_1$–$C_6$)-alkyl, ($C_1$–$C_6$)-alkyl;
n 0, 1, 2;
Q a group of the formula N(R24)(R25), or a nitrogen-containing 4 to 8-membered ring which, apart from the nitrogen atom, may also comprise a further 0–2 heteroatoms from the group of oxygen, nitrogen and sulfur, and where the ring system may additionally be substituted by N(R24)(R25), F, ($C_1$–$C_6$)-alkyl, O—($C_1$–$C_8$)-alkyl, ($C_0$–$C_4$)-alkoxy-($C_1$–$C_4$)-alkyl, ($C_0$–$C_8$)-alkylene-aryl, oxo, CO(R26), N(R30)CO($C_1$–$C_6$)-alkyl, or $SO_2CH_3$;
R24, R25 independently of one another H, ($C_1$–$C_8$)-alkyl, ($C_1$–$C_4$)-alkoxy-($C_1$–$C_4$)-alkyl, CO—($C_1$–$C_8$)-alkyl, or R24 and R25 form together with the nitrogen atom to which they are bonded a 4 to 8-membered monocyclic ring which, apart from the nitrogen atom, may include 0 or 1 additional heteroatoms selected from the group of oxygen, nitrogen and sulfur, where the heterocyclic ring system may additionally be substituted by ($C_1$–$C_6$)-alkyl, N(R48)CO($C_1$–$C_6$)-alkyl or N(R49)(R50);
R48, R49, R50 independently of one another H, ($C_1$–$C_6$)-alkyl;
R49 and R50 optionally together with the nitrogen atom to which they are bonded a 5–6 membered ring which, apart from the nitrogen atom, may also include 0–1 heteroatoms from the group of N—($C_0$–$C_6$)-alkyl, oxygen and sulfur;
R26, R30 independently of one another H, ($C_1$–$C_6$)-alkyl;
A a group of the formula —(C(R31)(R32))$_m$— in which one member may be replaced by an element from the group O, N(R33);
m 0, 1, 2, 3;
R31, R32, R33 independently of one another H, ($C_1$–$C_6$)-alkyl, aryl.

5. A compound of the formula I as claimed in claim 4, wherein D and G are each CH.

6. A compound of the formula I as claimed in claim 5, wherein
A is a group of the formula (C(R31)(R32))$_m$— in which 0–2 members may be replaced by an element from the group of O, N(R33), CO; preferably a group of the formula —(C(R31)(R32))$_m$— in which 1 member may be replaced by an element from the group of O, N(R33);
where
m is 1, 2, 3, 4; preferably 1, 3 or 4;
and
R31, R32, R33 are independently of one another H, ($C_1$–$C_6$)-alkyl, aryl; preferably H;
and
Q is N(R24)(R25);
where
R24, R25 are independently of one another H, ($C_1$–$C_8$)-alkyl, —(CH$_2$)$_n$—R36, CO—($C_1$–$C_8$)-alkyl, or R24 and R25 form together with the nitrogen atom to which they are bonded a 4 to 10-membered mono-, bi- or spirocyclic ring which, apart from the nitrogen atom, may include 0 to 2 additional heteroatoms selected from the group of oxygen, nitrogen and sulfur, where the heterocyclic ring system may additionally be substituted by F, Cl, ($C_1$–$C_6$)-alkyl, O—($C_1$–$C_8$)-alkyl, oxo, CO(R44), CON(R45)(R46), hydroxy, N(R48)CO($C_1$–$C_6$)-alkyl or N(R49)(R50), preferably F, ($C_1$–$C_6$)-alkyl, O—($C_1$–$C_8$)-alkyl, oxo, CO(R44), N(R48)CO($C_1$–$C_6$)-alkyl or N(R49)(R50);
o is 0, 1, 2, 3, 4;
R36 is OH, 5–10 membered mono- or bicyclic ring which may comprise one or more heteroatoms from the group of N, O and S, and the 5–10 membered ring may comprise further substituents such as F, Cl, Br, OH, $CF_3$, oxo, O—($C_1$–$C_6$)-alkyl, ($C_1$–$C_6$)-alkyl, O—($C_0$–$C_2$)-alkylene-aryl, ($C_0$–$C_2$)-alkylene-aryl and N(R55)(R56), preferably a 5–8 membered monocyclic ring which may comprise 0–2 heteroatoms from the group of N, O and S, and the 5–8 membered ring may comprise further substituents such as F, oxo, O—($C_1$–$C_6$)-alkyl, ($C_1$–$C_6$)-alkyl, ($C_0$–$C_2$)-alkylene-aryl and N(R55)(R56);
R44, R45, R46, R48, R49, R50 are independently of one another H, ($C_1$–$C_6$)-alkyl;
and
R55, R56 are independently of one another H, ($C_1$–$C_8$)-alkyl.

7. A compound of the formula I as claimed in claim 5, wherein
A is a group of the formula —(C(R31)(R32))$_m$— in which 0–2 members may be replaced by an element from the group of O, N(R33), CO; preferably a group of the formula —(C(R31)(R32))$_m$— in which 1 member may be replaced by an element from the group of O, N(R33);
where
m is 0, 1, 2, 3, 4; preferably 0 or 1;
and
R31, R32, R33 are independently of one another H, ($C_1$–$C_6$)-alkyl, aryl; preferably H;
where A very particularly preferably is a bond or N(R33);
and
Q is a 3 to 8-membered monocyclic ring which may include 0 to 3 heteroatoms selected from the group of oxygen, nitrogen and sulfur, where the ring system may additionally be substituted by F, Cl, Br, $CF_3$, $NO_2$, CN, ($C_1$–$C_6$)-alkyl, O—($C_1$–$C_8$)-alkyl, ($C_1$–$C_4$)-alkoxy-($C_1$–$C_4$)-alkyl, ($C_0$–$C_8$)-alkylene-aryl, oxo, CO(R26), CON(R27)(R28), hydroxy, hydroxy-($C_1$–$C_4$)-alkyl, COO(R29), N(R30)CO($C_1$–$C_6$)-alkyl or $SO_2CH_3$; preferably a 5 to 7-membered monocyclic ring which comprises one or two nitrogen atoms, where the ring system may additionally be substituted by ($C_1$–$C_6$)-alkyl, ($C_1$–$C_4$)-alkoxy-($C_1$–$C_4$)-alkyl or ($C_0$–$C_2$)-alkylene-aryl;
where
R26, R27, R28, R29, R30 are independently of one another H, ($C_1$–$C_6$)-alkyl; preferably ($C_1$–$C_6$)-alkyl.

8. A compound as claimed in claim 5, wherein
A is a group of the formula —(C(R31)(R32))$_m$— in which 0–2 members may be replaced by an element from the group of O, N(R33), CO; preferably a group of the formula —(C(R31)(R32))$_m$— in which 1 member may be replaced by an element from the group of O, N(R33);
where
m is 0, 1, 2, 3, 4; preferably 0 or 1;
and
R31, R32, R33 are independently of one another H, ($C_1$–$C_6$)-alkyl, aryl; preferably H;
where A very particularly preferably is a bond or N(R33);
and
Q is a 3 to 8-membered monocyclic ring which may include 0 to 3 heteroatoms selected from the group of oxygen, nitrogen and sulfur, where the ring system is additionally substituted by N(R24)(R25) and may additionally be substituted by F, Cl, Br, $CF_3$, $NO_2$, CN, ($C_1$–$C_6$)-alkyl, O—($C_1$–$C_8$)-alkyl, ($C_1$–$C_4$)-alkoxy-($C_1$–$C_4$)-alkyl, ($C_0$–$C_8$)-alkylene-aryl, oxo, CO(R26), CON(R27)(R28), hydroxy, hydroxy-($C_1$–$C_4$)-alkyl, COO(R29), N(R30)CO($C_1$–$C_6$)-alkyl or $SO_2CH_3$; preferably a 3 to 8-membered monocyclic ring which may include 0 to 1 heteroatom selected from the group of oxygen, nitrogen and sulfur, where the ring system is additionally substituted by N(R24)(R25) and may additionally be substituted by F, Cl, Br, $CF_3$, $NO_2$, CN, ($C_1$–$C_6$)-alkyl, O—($C_1$–$C_8$)-alkyl, ($C_1$–$C_4$)-alkoxy-($C_1$–$C_4$)-alkyl, ($C_0$–$C_8$)-alkylene-aryl, oxo, CO(R26), CON(R27)(R28), hydroxy, hydroxy-($C_1$–$C_4$)-alkyl, COO(R29), N(R30)CO($C_1$–$C_6$)-alkyl or $SO_2CH_3$, preferably F, ($C_1$–$C_6$)-alkyl, O—($C_1$–$C_8$)-alkyl, ($C_1$–$C_4$)-alkoxy-($C_1$–$C_4$)-alkyl, ($C_0$–$C_8$)-alkylene-aryl, oxo, CO(R26), N(R30)CO($C_1$–$C_6$)-alkyl or $SO_2CH_3$;

where

R26, R27, R28, R29, R30 are independently of one another H, ($C_1$–$C_6$)-alkyl; preferably ($C_1$–$C_6$)-alkyl; and R24, R25 are independently of one another H, ($C_1$–$C_8$)-alkyl, —$(CH_2)_o$—R36, CO—($C_1$–$C_8$)-alkyl, or R24 and R25 form together with the nitrogen atom to which they are bonded a 4 to 10-membered mono-, bi- or spirocyclic ring which, apart from the nitrogen atom, may include 0 to 2 additional heteroatoms selected from the group of oxygen, nitrogen and sulfur, where the heterocyclic ring system may additionally be substituted by F, Cl, ($C_1$–$C_6$)-alkyl, O—($C_1$–$C_8$)-alkyl, oxo, CO(R44), CON(R45)(R46), hydroxy, N(R48)CO($C_1$–$C_6$)-alkyl or N(R49)(R50), preferably F, ($C_1$–$C_6$)-alkyl, O—($C_1$–$C_8$)-alkyl, oxo, CO(R44), N(R48)CO($C_1$–$C_6$)-alkyl or N(R49)(R50);

o is 0, 1, 2, 3, 4;

R36 is OH, 5–10 membered mono- or bicyclic ring which may comprise one or more heteroatoms from the group of N, O and S, and the 5–10 membered ring may comprise further substituents such as F, Cl, Br, OH, $CF_3$, oxo, O—($C_1$–$C_6$)-alkyl, ($C_1$–$C_6$)-alkyl, O—($C_0$–$C_2$)-alkylene-aryl, ($C_0$–$C_2$)-alkylene-aryl and N(R55)(R56), preferably a 5–8 membered monocyclic ring which may comprise 0–2 heteroatoms from the group of N, O and S, and the 5–8 membered ring may comprise further substituents such as F, oxo, O—($C_1$–$C_6$)-alkyl, ($C_1$–$C_6$)-alkyl, ($C_0$–$C_2$)-alkylene-aryl and N(R55)(R56);

R44, R45, R46, R48, R49, R50 are independently of one another H, ($C_1$–$C_6$)-alkyl; and R55, R56 are independently of one another H, ($C_1$–$C_8$)-alkyl.

9. A process for preparing compounds as claimed in claim 1, whose A–Q group is linked via a nitrogen atom to the cyclohexylene ring, comprising the steps of a) preparation of a compound of the formula II

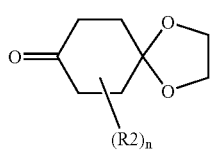

II b) reaction of the compound of the formula II with

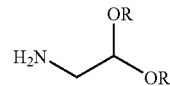

under reductive amination conditions, where R=lower alkyl, preferably ethyl or methyl, to give a compound of the formula III

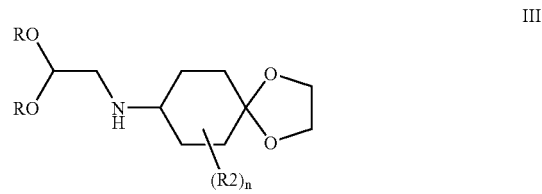

III c) coupling of the compound of the formula III with phosgene (or a known phosgene equivalent, for example carbonyldiimidazole) and a primary amine of the formula

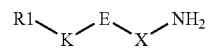

and subsequent deprotection of the acetals, with simultaneous cyclization resulting in a compound of the formula IV

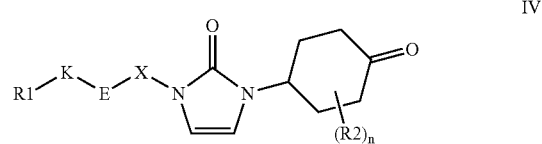

IV d) reaction with a primary or secondary amine under reductive amination conditions, resulting in compounds of the formula I whose A–Q group is linked via a nitrogen atom to the cyclohexylene ring

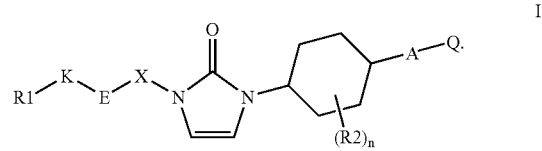

I

10. A medicament comprising one or more of the compounds as claimed in claim 1.

11. A medicament comprising one or more of the compounds as claimed claim 1 and one or more anorectic active ingredients.

12. A process for producing a medicament comprising one or more of the compounds of the formula I as claimed in claim 1, which comprises mixing the active ingredient with a pharmaceutically acceptable carrier and converting this mixture into a form suitable for administration.

13. A method for reducing weight in mammal comprising administering to a mammal in need thereof an amount of a compound of formula I as claimed in claim 1 necessary to achieve weight reduction.

14. A method for treating obesity comprising administering to a mammal in need thereof an amount of a compound of formula I as claimed in claim 1 necessary to treat obesity.

15. A method for the treatment of type II diabetes comprising administering to a mammal in need thereof an amount of a compound of formula I as claimed in claim 1 necessary to treat type II diabetes.

* * * * *